United States Patent
Glasgow, Jr. et al.

(10) Patent No.: US 7,040,157 B2
(45) Date of Patent: May 9, 2006

(54) VARIABLE DEPTH AUTOMATED DYNAMIC WATER PROFILER

(75) Inventors: Howard Glasgow, Jr., Bahama, NC (US); Robert E. Reed, Raleigh, NC (US); David C. Toms, Raleigh, NC (US); JoAnn Burkholder, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 569 days.

(21) Appl. No.: 10/208,504

(22) Filed: Jul. 30, 2002

(65) Prior Publication Data

US 2003/0037602 A1     Feb. 27, 2003

Related U.S. Application Data

(60) Provisional application No. 60/309,001, filed on Jul. 31, 2001.

(51) Int. Cl.
*G01C 13/00* (2006.01)
*G01N 11/00* (2006.01)

(52) U.S. Cl. .................... 73/170.29; 73/53.01
(58) Field of Classification Search ............ 73/61.41, 73/53.01, 170.29
See application file for complete search history.

(56) References Cited

U.S. PATENT DOCUMENTS

| | | | |
|---|---|---|---|
| 3,394,583 A * | 7/1968 | Dongherty, Jr. et al. ... | 73/24.01 |
| 3,432,656 A * | 3/1969 | Smith et al. ........... | 250/363.01 |
| 3,656,342 A * | 4/1972 | Peep et al. ............. | 73/170.31 |
| 3,782,692 A * | 1/1974 | Casco et al. ............ | 242/387 |
| 3,968,954 A * | 7/1976 | Casco et al. ............ | 254/332 |
| 4,157,657 A | 6/1979 | Hinchman .............. | 73/53 |
| 4,662,210 A | 5/1987 | D'Aoust ................ | 73/19 |
| 4,924,698 A * | 5/1990 | Echert et al. .......... | 73/170.29 |
| 5,264,906 A * | 11/1993 | Ferer et al. ........... | 356/28 |
| 5,606,138 A | 2/1997 | Saarenketo ............ | 73/864.34 |
| 5,816,874 A | 10/1998 | Juran et al. ............ | 441/1 |
| 5,821,405 A | 10/1998 | Dickey et al. ......... | 73/53.01 |
| 5,869,756 A * | 2/1999 | Doherty et al. ........ | 73/170.29 |

(Continued)

FOREIGN PATENT DOCUMENTS

DE     296 08 551 U1     9/1996

(Continued)

OTHER PUBLICATIONS

Kuwano et al., New Multimedia Communication Services Using sensing Systems, Development of Water-Quality Sensing Network System, NTT Review, XP000643777, vol. 9, No. 1, Jan. 1997, pp. 100-107.

(Continued)

*Primary Examiner*—Hezron Williams
*Assistant Examiner*—John Fitzgerald
(74) *Attorney, Agent, or Firm*—Myers Bigel Sibley & Sajovec PA

(57) ABSTRACT

A winch-based system is used to raise and lower a hydrological probe into a water column to automatically dynamically obtain measurement data of a water column at incremental depths over selected time intervals. The winch-based system can be powered by a relatively low-power power source to cause the electric motor to controllably operate to wind and unwind the cable at a desired rate in a manner which can pause the upward and downward movement of the probe at incremental measurement depths. The disclosure also describes related systems. Additionally, a method for enhancing the life of a hydroglogical probe by storing the probe at an immersed subsurface depth is also described.

43 Claims, 22 Drawing Sheets

U.S. PATENT DOCUMENTS

2003/0092393 A1* 5/2003 Tokhtuev et al. .......... 455/67.1

FOREIGN PATENT DOCUMENTS

| DE | 196 26 262 A1 | 1/1998 |
|----|---------------|--------|
| FR | 2 721 113 | 6/1994 |
| WO | WO 93/17334 | 9/1993 |
| WO | WO 96/29597 | 9/1996 |

OTHER PUBLICATIONS

Pitchai et al., Design of a Synoptic Water Quality Monitoring System for Narragansett Bay, IEEE Transactions on Geoscience Electronics, XP002237715, Jan. 1972, pp. 17-24.

Torán et al., Design of a Virtual Instrument for Water Quality Monitoring Across the Internet, Sensors and Actuators B 76 (Jun. 1, 2001) pp. 281-285.

PCT International Search Report, International Application No. PCT/US02/24011 dated Apr. 25, 2003.

Russ Dynamic Profiler, Apprise Technologies, Inc., www.apprisetech.com, 2 sheets (date believed to be before Jul. 2001).

Seakeepers Ocean Monitor Gets US Patent, 1 sheet of screen printout, OceanSpace No. 469, Jan. 2003.

In-Well Monitoring System for Vertical Profiling of DNAPL Contaminants, TMS Tech ID: 3157, pp. 95-96, Sep. 2002.

Seakeeper Field Testing Program, 2 sheets of screen printouts, www.seakeepers.org/technology/fieldtesting.htm, (date of some actions believed to be before Jul. 2001).

Seakeepers Module Specifications, two sheets of screen printouts, www.seakeepers.org/technology/modulespecs.htm (copyr. 2001).

Seakeepers Module Specifications, lower module, 1 sheet screen print out, www.seakeepers.org/technology/lowermodule.htm (copyr 2002, use of prototype believed to be before Jul. 2001).

Seakeepers Research and Development, 2 sheets screen printouts, www.seakeepers.org/technology/md.htm (believed to describe pre-2001 activity).

Idronaut Systems including Profiler Module of 601 and 701 buoy supports, 10 sheets of screen printouts, www.idronaut.it/boa/main4html and others as noted on sheets, date unknown but believe describes products available before 2001.

Idronaut Company Profile notint marine instrumentation available and awards between 1989-1993, www.idronaut.it/company/company.html.

Frommichen et al, Chlorophyll Maxima-explanation for resource management of the phytoplankton in acidic open pit mining lake, 1 sheet, unknown date but describes 1999 depth profile in Figure 3 and shows Idronaut profiling probe in Figure 1.

Nyffeler et al., A practical comparison between Seabird SBE911 and Ocean Seven 320 CTD Probes, 3 sheets, date unknown but describes summary of pre-2001 probes.

Free Fall Profiler Winch BOT, Brooke Ocean Technology, Ltd, 8 sheets of screen printouts, www.brooke-ocean.com/ffwinch.html (date of free fall winch believed to be 1998, copyr. 2002).

Instrumented Metering Sheave, 5 sheets of screen printouts, www.brooke-ocean.com/imsheave.html, (copyr. 2002, date unknown).

Bedford Institute and Brooke Ocean Technology Develop Novel Sensor Platforms, BOT Press Release, two sheets describing MVP Profiler and Seahorse profiler, Feb. 1998.

Three Recent Moving Vessel Profiler (MVP) Deliveries for Brooke Ocean Technology, BOT Press Release, two sheets describing MVP profiler, Mar. 28, 2001.

News Releases, 2 sheets, BOT Summary of releases from 1998-2002, ww.brooke-ocean.com/PressReleases.html.

OS5000 APV Winch/Slider/Mooring Configuration diagrams, 3 sheets of screen printouts, www.oceansensors.com, copyright 2001.

* cited by examiner

VARIABLE DEPTH AUTOMATED DYNAMIC WATER PROFILER

RELATED APPLICATIONS

This application claims priority from U.S. Provisional Patent Application Ser. No. 60/309,001, filed Jul. 31, 2001, the contents of which are hereby incorporated by reference as if recited in full herein.

FIELD OF THE INVENTION

The present invention relates to systems and methods for monitoring water quality at various depths.

BACKGROUND OF THE INVENTION

Conventionally, manual collection of water samples have been used to assess or measure one or more parameters of interest associated with water quality. Unfortunately, manual collections can be time-consuming and laborious and the sample may be inconsistently obtained at relatively long intervals between collections and/or at different depths in the water column, potentially reducing the value of the information.

In the past, many users have chosen to suspend a probe or sensor from the side of a piling, platform, or buoy to allow readings to be obtained at desired points in time. Commercially available sensors can monitor several parameters with a single integrated probe. These parameters include pH, temperature, turbidity, conductivity, dissolved oxygen, and chlorophyll. Examples of these type of multi-sensor probes include those available from HydroLab Corporation located in Austin, Tex., and other sources such as YSI, Sea-Bird, Wet Labs, Li-Cor, and the like.

One commercial automated water monitoring system, known as the R.U.S.S. Dynamic Profiler™, available from Apprise Technologies, Inc., uses a variable buoyancy technique to raise and lower a multi-sensor probe at selected time intervals and collect water quality data in a water column, allegedly to a depth of about 100 m. The buoyancy-based system can collect the water quality data daily at selected times or upon demand. The collected data can then be forwarded to a remote or central location using various known communication techniques such as cellular, satellite or VHF technology. See Url www.apprisetech.com for additional description of profilers such as that noted above. See also U.S. Pat. Nos. 5,816,874 and 5,606,138 for additional examples of adjustable buoyancy water sampling systems and/or communication transfers between the testing site and a central station; the contents of these patents are hereby incorporated by reference as if recited in full herein.

However, despite the above, conventional automated water quality profiling systems can be relatively expensive, may require undue amounts of power, or may need an undesirable amount of maintenance, and further may not be able to measure the condition of the water at surface level (particularly when monitoring bodies of water having variable water levels). Further, the operation, of known water monitoring systems may unduly shorten the useful life of the probe or sensor used. There remains a need to provide improved low cost alternatives for automated dynamic monitoring of water quality.

SUMMARY OF THE INVENTION

The present invention provides a relatively low cost winch-based alternative to conventional systems. The present invention can be added to many many existing water monitoring systems that employ hydrological probes with little modification. In certain embodiments, the system can operate such that it is surface level intelligent (i.e., it can adjust each profile reading so as to indicate fluctuation in water level (change in depth) and/or obtain a reading at the actual surface level).

In certain embodiments, the present invention is directed to a method for dynamically monitoring at least one parameter of interest in a liquid environment using a hydrological probe which is attached to a cable mounted on a spool of a winching system. The winching system can controllably unwind a quantity of cable to lower a hydrological probe into a liquid environment at a series of increasing incremental distances away from the surface of the liquid. First data measurements can be obtained for at least one selected parameter of interest in the liquid environment at the selected distances. Second data measurements can be obtained for the at least one selected parameter of interest in the liquid environment at the selected distances after the first measurements. The liquid environment can be monitored to generate a time-dependent dynamic liquid profile of the at least one parameter of interest based on the first and second data measurements.

In other embodiments, instead of lowering the probe, the sampling can be carried out by raising the hydrological probe in a liquid environment (winding the cable upward) at a series of increasing incremental distances above the bottom of the liquid by winching the cable to controllably wind a quantity of the cable attached thereto and then serially obtaining over a desired interval of time the first and second data measurements for the at least one selected parameter of interest in the liquid environment at the selected distances or depths.

In certain embodiments, whether by raising or lowering the probe, the winching can be powered by a low voltage power source and the second obtaining step can be initiated at between about 1–12 hours from the first obtaining step. The liquid environment may be a body of water, and the first and second obtaining steps can be automatically carried out so as to generate water profile data measurements at about 3 hour intervals for a desired monitoring period (such as 1 week, 1 month, or longer). The sampling interval is adjustable (user programmable) and measurements can be taken at any suitable time, subject to the travel time of the water quality probe (sonde) and number of sampling positions during the data collection.

In certain embodiments, the probe can be lowered or raised such that the hydrological probe ascends or descends for about 30 seconds, and then pauses to dwell at a second depth to take a measurement, continues for about another 30 seconds to a third depth, pauses to take a measurement at the third depth, continues for about another 30 seconds to a fourth depth, and then pauses to take a measurement at the fourth depth.

In other embodiments, the data measurements include taking a reading at the surface of the liquid even in variable height liquid environments.

Other embodiments of the present invention are directed to a method for enhancing the life of a hydrological probe. The method includes: positioning a hydrological probe in a body of water; measuring at least one parameter of interest of the water at a plurality of depths of the body of water over time with the hydrological probe; and storing the probe such that it is held immersed in the body of water at a subsurface depth after the measuring step (such as during inactive measurement periods). In certain embodiments, the subsurface depth may be at a depth adjacent the bottom of the body of water.

Still other embodiments of the present invention include a kit for an automated water profiler system. The kit can include a winching system having a drum with a length of multi conductor cable configured to wind thereon. The mutli-conductor cable is adapted to engage with a hydrological multi-sensor probe. The kit can also include a low voltage power source adapted to be in electrical communication with the winching system during use and an electric motor operably associated with the power source and the winching system. The kit can also include a controller adapted to be in communication with the power source, the electric motor, and the winching system during operation. The kit includes means for selectively powering the motor at desired intervals to activate the winching system so as to obtain a series of data measurements from the probe at a plurality of depths in a water column during use. The means can include, but is not limited to electro-mechanical components and/or a computer program.

In certain embodiments, the kit can include a guide tube configured to be disposed in a body of water and to receive the probe therein to direct the travel direction of the probe. The kit may also include means for causing the probe to be stored in the bottom of the water column during periods of inactivity (such as an electro-mechanical subsystem and/or a computer program). Of course other components may be added or altered in the modification kit.

Other embodiments are directed to automated water profiler systems and include: a controller; a winching system having a drum with a length of multi conductor cable, the mutli-conductor cable adapted to engage with a hydrological mutli-sensor probe; a power source configured to be in electrical communication with the winching system; an electric motor configured to be operably associated with the power source and the winching system; and means for selectively powering the motor at desired intervals to activate the winching system so as to automatically obtain a series of data measurements from the probe at a plurality of depths in a water column. The system can be configured to controllably wind and unwind the cable at desired time intervals and to cause the probe to be held submerged during periods of inactivity. In addition, the system can include correcting operational features to: (a) self-correct or reset the probe depth or location when sensors or switches indicate it is not at a proper level; and (b) activate remote alarms when certain predetermined conditions are identified.

Other embodiments are directed to automated water profiler systems for monitoring a body of liquid. The systems include: (a) a winching system having a drum wound with a length of cable, the cable adapted to engage with a hydrological multi-sensor probe; (b) a power source configured to be in electrical communication with said winching system; (c) an electric motor configured to be operably associated with the power source and the winching system; (d) a controller in communication with a relay circuit for selectively controllably powering the motor at desired intervals to activate the winching system so as to automatically obtain a series of data measurements from the probe at a plurality of depths in a liquid column (the system is configured to controllably wind and unwind the cable at desired time intervals to obtain time-dependent data of at least one selected liquid parameter); and (e) a wireless communication means operably associated with the controller for receiving commands from a remote monitoring site and dynamically transmitting data measurements thereto in substantially real-time.

In yet other embodiments, the present invention is directed to a network of automated water profiler system for monitoring a body of water, comprising a plurality of distributed automated water profilers, each including those features described above and at least one remote data acquisition site configured to generate and transmit commands to, and receive data from, each of the automated water profilers. The remote data acquisition site comprises a controller that evaluates the data from each of the distributed automated water profilers and generates trend analysis data of selected hydrological parameters over time.

Objects of the present invention will be appreciated by those of ordinary skill in the art from a reading of the figures and the detailed description of embodiments of the invention that follow, such description being merely illustrative of the present invention.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 12A illustrates the wind conditions (direction and speed) over a selected time period. FIG. 12B illustrates salinity (PSU) at a first site located at the north shore of Kennel Beach over a corresponding time period (shown in Julian Day). The side legend defines the levels of salinity corresponding to the gray scale shown. FIG. 12C illustrates similar data for a second site located at the south shore of Carolina Pines. The "0" level shown is for the bottom of the water column shown as the top of the graph.

FIG. 13B illustrates the gradient measured at the north shore of Kennel Beach and FIG. 13C illustrates measurements taken at the south shore at Carolina Pines.

FIGS. 14B and 14C are graphs of salinity measured in the water column at the north shore of Kennel Beach and the south shore of Carolina Pines, respectively.

FIG. 15B illustrates the measurement results taken at the north shore of Kennel Beach and FIG. 15C illustrates the measurement results taken at the south shore of Carolina Pines.

DETAILED DESCRIPTION OF EMBODIMENTS OF THE INVENTION

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, certain regions, components, features or layers may be exaggerated for clarity. Broken lines in the figures indicate that the feature or step so indicated is optional unless noted otherwise.

Figure 1A:
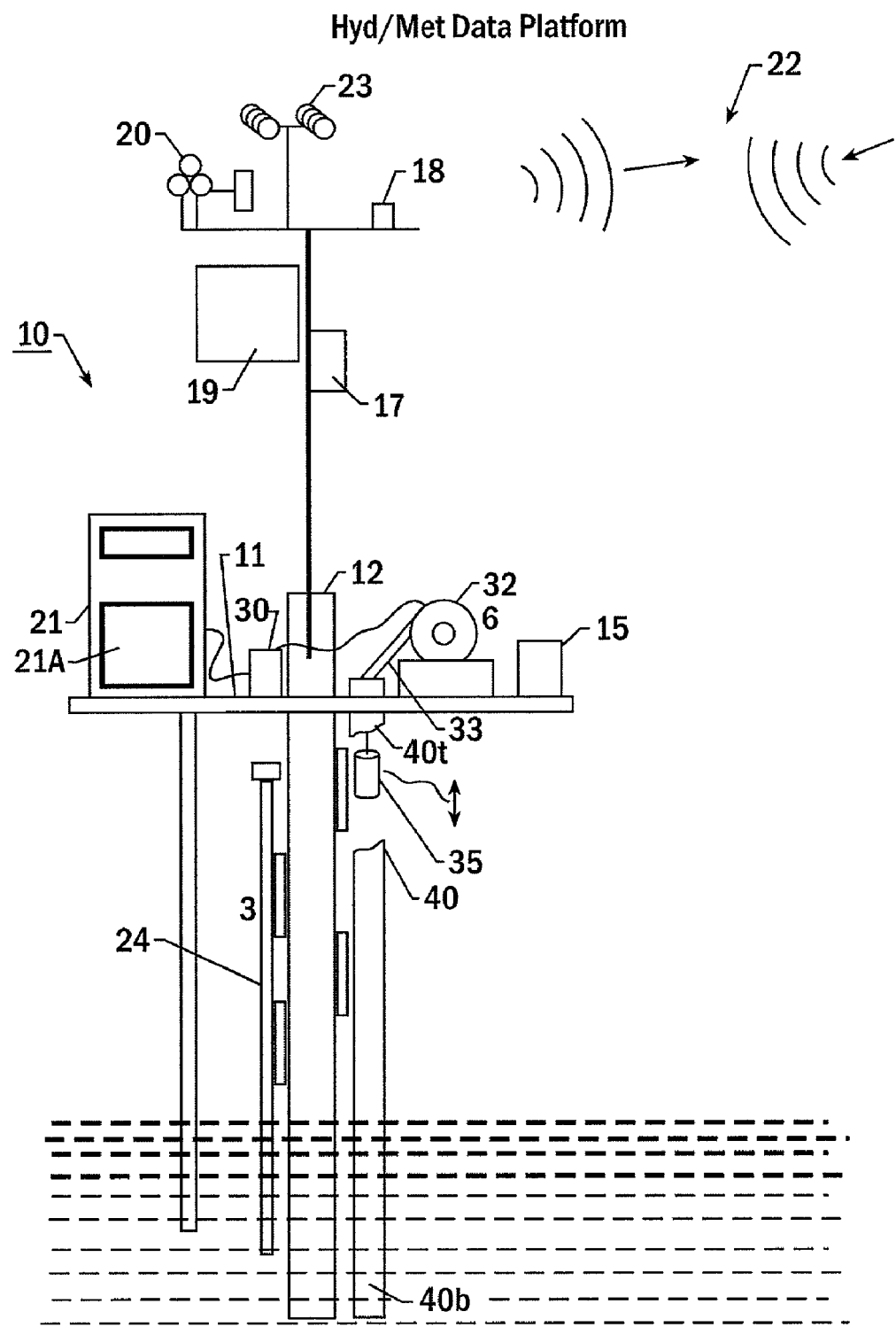
FIG. 1A is a schematic illustration of an automated water profiler system according to embodiments of the present invention.

Turning to FIG. 1A, one embodiment of an automated dynamic water quality monitoring system 10 according to the present invention is shown. In the embodiment shown, the water quality monitoring system 10 includes a platform 11 mounted to a piling 12 which is anchored or driven into material at the bottom of a body of water and used to position the water quality monitoring system 10 at a desired marine location. For ease of description, the water quality system 10 will be shown as being mounted to a stationary platform. However, the system 10 need not be mounted to a stationary platform, and can, alternatively, be mounted to a floating platform, boat, or a buoy as desired. In addition, the system can be mounted to existing structures located in the body of water or liquid for which automated multi-depth evaluation is desired, such as oil platforms, telecommunication towers and the like. The system may be particularly suitable for monitoring bodies of water such as fresh water including lakes, and rivers, or salt or brackish water, including oceans, intercoastal waterways, estuaries, canals, marsh land, swamps, and deltas. In certain embodiments, a plurality of automated systems 10 may be dispersed in locations in a related flowing body of water such as along the path of a river and at the junction of rivers into ocean waters (ocean inlets). The system 10 may also be used in other liquid environments including wastewater plants, sewer systems, tanks, wells or drinking water systems.

In certain embodiments, the water monitoring system 10 is configured to dynamically monitor both hydrological and meteorological conditions. This can allow the weather conditions at the monitoring site to be correlated to the water conditions at the monitoring site. As shown in FIGS. 1A and/or 1B to monitor meteorological and other parameters such as environmental (liquid and/or air) nutrient conditions, the system 10 can include a rainfall sensor 15, a relative humidity sensor 17, a sunlight intensity sensor 18, a housing enclosure for experimental sensors or equipment 16, and wind/speed direction sensors 20. In addition, the system 10 can include a computer 21 and wireless communication means 22 (outgoing and incoming) to allow the monitoring system 10 to be controlled from a remote site and/or to upload or transfer the collected or measured water profile data and/or meteorological data at desired intervals (whether at default or selected times and/or upon demand). The wireless communication means can be radio wave transmission, cellular, digital, and/or satellite signal relay transmission, or a combination of same. The system 10 can, alternatively be configured to operate and/or communicate via hardwired or dedicated lines as well (including, for example, but not limited to, fiber optic, cable, ISDN, or telephone lines). Combinations of the above are also possible.

As is also shown in FIG. 1A, the system 10 also includes a power source 30, a hydrological probe winching system or winch 32, cable 33, and a hydrological probe 35. The system 10 is configured to operate the winch 32 to wind and unwind the cable 33 to thereby lower and raise the hydrological probe 35. These components will be discussed further below.

In certain embodiments, the system 10 can also include a guide pipe 40 that is held at a desired orientation to define the desired travel path. Typically, the guide 40 is mounted securely to the bottom of the body of water undergoing analysis in a substantially vertical orientation to define a vertical travel path for the probe 35. In other embodiments, the guide 40 can be positioned above the bottom of the body of water and held in position by an anchoring unit and/or cabling which is securely implanted or attached to the bottom. Similarly, the guide 40 may extend to a location adjacent the bottom of the platform 11 or above the platform 11, or at other positions below the platform 11 as desired. In certain embodiments, the guide 40 extends a sufficient distance above the water to retain the probe 35 therein as the probe 35 surfaces to take a surface reading. The guide 40 can be located such that it is in predetermined spaced horizontal and/or vertical alignment with the winching system 32. The guide 35 can be sized and configured to surround and to hold the hydrological probe 35 so that it is captured laterally to guide the hydrological probe 35 in a desired sensing path (typically a substantially vertical column). The bottom and/or top of the guide 40*b*, 40*t* may be open or may be closed. If it includes a closed top 40*t*, it may be desirable to include a releasable portion or member (typically above the surface) from which to access or interchange the probe 35 during service or repair or to position during set-up. If the top 40*t* is closed, a suitable cable aperture can be formed therein to allow the cable 33 to travel therethrough. The bottom portion 40*b* (or other axially spaced selected portions) can be configured with a relay or relays that cooperate with the probe 35 to contact and transmit a signal to the system 10 to indicate that the probe 35 has reached the desired depth or position. This can be the storage or end position or various depths along the water column to help confirm that the depth meter is calibrated to the sampling depth. The guide lower end portion 40*b* can be configured to securely hold the probe 35 during periods of inactivity to inhibit contact damage with the tube (or other peripheral items). The guide lower end portion 40*b* may also be configured with a probe sensor life-prolonging surface or cavity which can receive the lower edge of the probe 35 and introduce an antifouling or cleansing material at desired intervals via a line in fluid communication with the lower portion of the guide (or cavity) extending from the platform 11 to the guide and configured to direct the material into the cavity (not shown). The guide 40 can be a PVC (polyvinylchloride) pipe which may be coated with a marine coating material to inhibit marine growth thereon. A suitable coating is known as Interlux, Fiberglass Bottomkote® ACT, part no. 7740, from Ablative Copolymer Technology, Union, N.J.

Figure 1B:
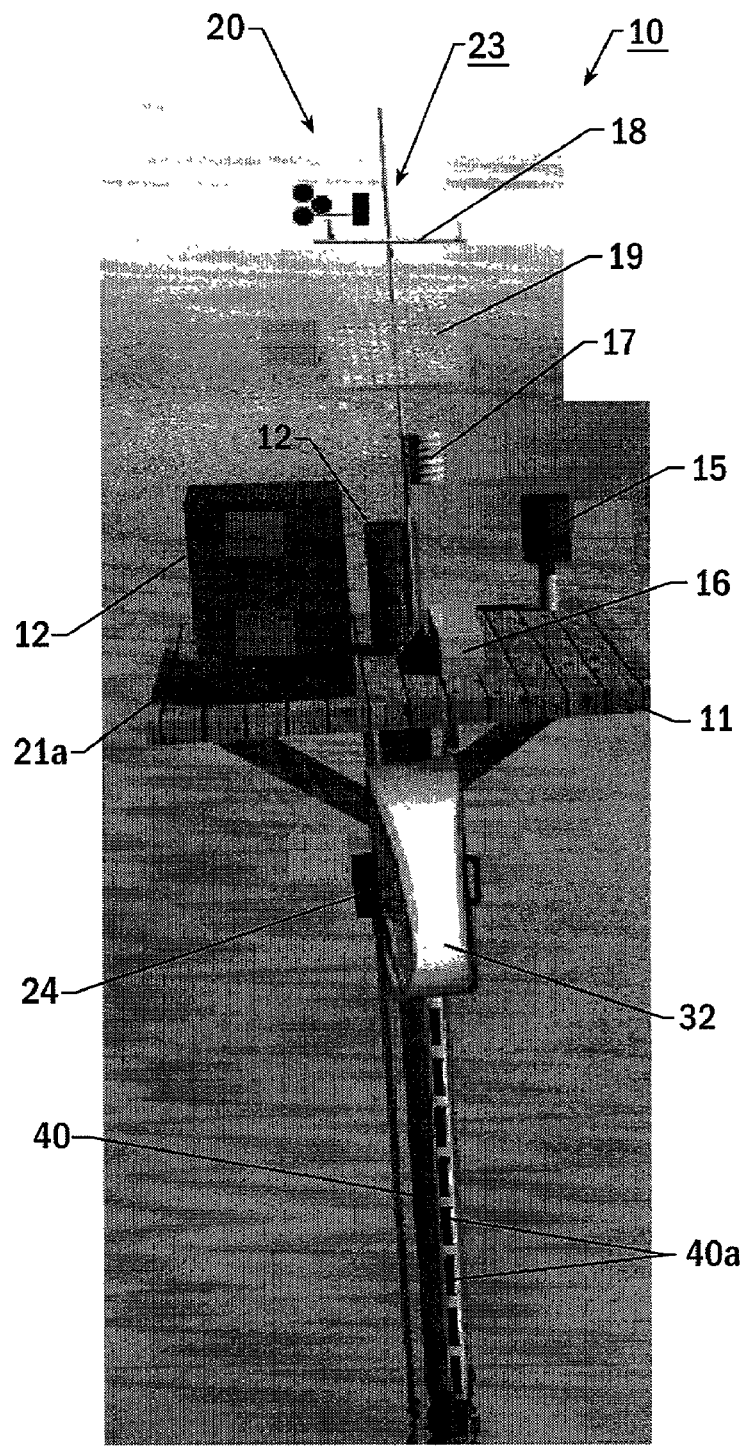
FIG. 1B is a schematic illustration of another automated water profiler system according to embodiments of the present invention.
Figure 2A:
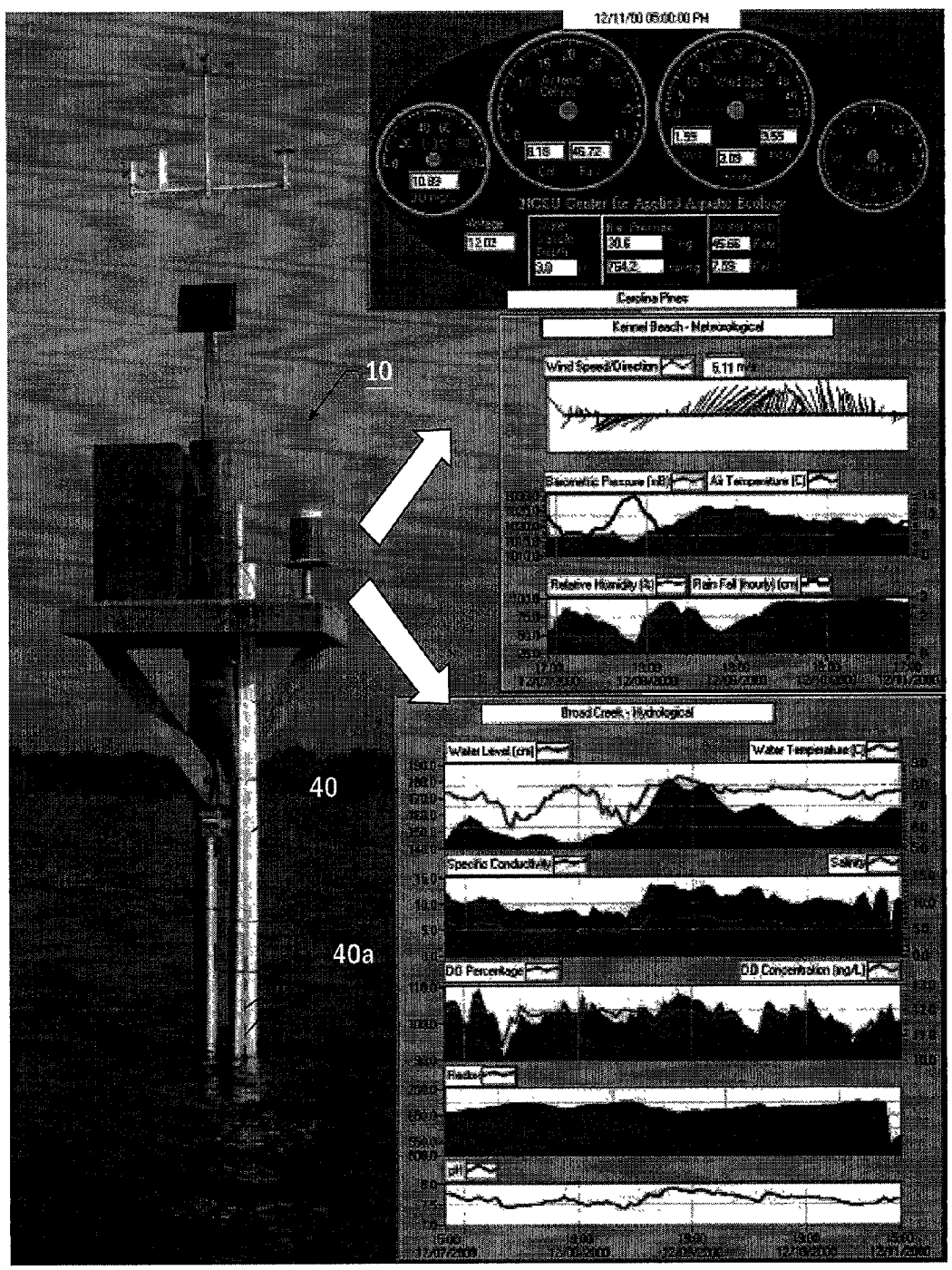
FIG. 2A is a photograph of an automated water profiler system according to embodiments of the present invention positioned adjacent exemplary screen displays or print outs of reports of selected monitored parameters over time according to embodiments of the present invention.

As shown in FIGS. 1B and 2A, the guide tube 40 can include a plurality of apertures 40*a* formed into the tube 40. The apertures 40*a* can be configured in size and arranged in location about the length of the guide tube 40 to allow water representative of the water at the incremental measurement depths to enter therein. As shown, the guide tube 40 is cylindrical and the apertures are circumferentially spaced about the perimeter of the guide tube 40 at a plurality of axially spaced positions along the length of the guide tube. In the embodiment shown, the apertures 40*a* are configured as axially elongated slots. Other configurations can also be employed.

In operation, the hydrological probe 35 is positioned in the guide tube 40 so that the hydrological probe 35 travels up and down a length of the guide tube 40 during the lowering and raising of the cable as the winch 32 unwinds or winds the cable 33, respectively. In certain embodiments, the apertures 40*a* are arranged to extend a distance above the water line but a major distance below the platform 11 intermediate the platform and water level. The apertures 40*a* can be formed into the guide tube 40 at each desired measurement depth. The winch 32 can selectively or controllably raise and lower the probe 35 so that the probe dwells or pauses a period at each measurement depth before continuing to the next measurement depth.

The system 10 can also include a solar panel 19 (FIGS. 1A, 1B) to provide supplemental power or re-charging energy for one or more of the devices or sensors located on the platform 11. In addition, the platform 11 may also include a lightening protection member 23. In certain embodiments, the system 10 can include a water level sensor 24 such as, but not limited to, a pressure water level sensor, to dynamically define the water level at the surface of the water. The water level sensor 24 can be any desired level sensor type suitable for detecting fluctuating water levels whether as a stationary sensor attached to the piling 12 or platform 11 or attached to adjacent structures (such as the guide tube). The water level sensor 24 can be, but is not limited to, a conventional strip water level sensor, an infrared sensor(s), or a floating sensor.

The water level sensor 24 can provide dynamic water level data which can be monitored by the system 10 so that the system is "surface level intelligent"; it can be used to define where the surface level is to allow the hydrological probe 35 to have a variable surface measurement location so that it can take a measurement at the surface no matter where that surface may be during the sampling run or monitoring period. This can be particularly useful in locations with variable water levels due to tidal conditions, the release of water from dams, high winds, and/or various natural weather conditions (such as heavy rains, hurricanes, tropical depressions, storms, and the like) that may influence the water table. As such, the system 10 can measure parameters at surface of variable height water and can define the surface level to adjust where the system begins/ends its readings and note at what level to allow the variable water level and readings to be dynamically correlated over time. In addition, a fish finder or other desired detector as well as other desired sensors can also be included with the system (not shown).

Although shown as a single computer 21, multiple computers or signal processors such as master/slave processors can be configured to operate the system 10. The computer 21 can be configured with an automated water sampler module 21A to control the operation of the winch 32 and the hydrological probe 35.

In operation, the hydrological probe 35 is lowered or raised via a winch 32 to a plurality of incrementally increasing or decreasing depths in the water column. In certain embodiments, at each of the plurality of measurement depths in the water column, the probe may pause and obtain the reading, at which time the probe is lowered to the next desired measurement depth. In other embodiments, the samples may be measured as the probe continues its descent or ascent.

FIG. 1B illustrates that the winch system 32 can be a relatively compact modular configuration that can be mounted under the platform 11 or on a side of a piling (without a platform) above the water level. The system 10 can be configured to be a substantially real-time remote monitoring system that acts alone, or as a data collection point in an integrated system of a plurality of such stations or systems 10. The system can obtain and relay information to a remote monitoring site that can broadcast or relay the data to a computer network, such as a global computer network.

The winch 32 can be powered by a motor 32M (FIG. 3), which can raise or lower the probe 35 at a desired rate of speed. In certain embodiments, the rate of speed can be from about 0.02 m/s to about 2.0 m/s. The winch 32 may also be configured to pause or dwell for about 10 seconds to 2 minutes or longer to obtain the desired readings at each of the desired measurement depths. This sequence can be repeated until the entire water column has been sampled. In certain embodiments, the winch 32 can be powered to move the probe 35 in the desired direction for about 30 seconds (corresponding to a depth increment of about 0.5 m) and then paused for about 90 seconds to obtain the reading. For a typical site (using about 30–80 feet of cable), the entire water column can be sampled in about 20–60 minutes. For example, the system 10 can be operated to take readings at 10 incremental depths in a water column having a depth of 5–20 m, at every 0.5–1 m depth, the water profile measurements can occur over an elapsed 20–40 minute sampling cycle (the time from the first to the last reading). The sampling cycle can vary depending on the extension/uptake rate, the dwelling period for measurement at each measurement depth, and the number of different measurement depths sampled. In certain embodiments, the system can wind and unwind about 30–80 feet of cable at a rate of about 0.2 m/minute.

In certain embodiments, the system 10 is configured as a low torque system to sample water columns of less than about 80–100 feet using a continuous sampling interval of about every 1–12 hours. The sampling intervals (lowering depths, times, pauses, and the like) can be user defined and programmably set at or prior to installation and/or adjusted during operation. Thus, for example, in operation, the system 10, 10' can lower the hydrological probe at a first user defined interval, pause to take a measurement at the first lowered depth, continue to lower for about a second user defined interval to a second lowered depth, pause to take a measurement at the second lowered depth, continue for about third user set interval to a third lowered depth, and then pause to take a measurement at the third lowered depth. Additional numbers of sampling at additional depths can be carried out depending on the desired number of data collection points desired. The first, second, and third intervals can be adjustable (sampling cycle to sampling cycle, day to day, or at other desired adjustment periods) and can adjust the sampling depths as desired. In addition, the sampling depths for a sampling cycle or for each sampling cycle may be at equal depth increments or different depth increments. The user defined interval can be adjusted or set in situ at one or more monitoring sites, may be programmed or defined during operational set-up prior to field installation, and/or may be adjusted at the monitoring site by the data acquisition computer at the shore site. In particular embodiments, the user defined intervals may be set to be at about every 30 seconds to about every five to ten minutes in a sampling cycle.

In particular embodiments, the system 10, 10' can be configured to sample depths of about 40 feet. In certain embodiments, a low torque system can include a motor that is configured to operate with about 50 in-lbs of torque. The low torque motor may be configured to operate at about 0.30–15.0 rpm. In particular embodiments, the motor can operate at either about 0.45 rpm or about 5.0 rpm, depending on commercially available motors that meet the operational parameters (to control production costs). The motors may operate with about $\frac{1}{1200}$ HP on a 12 VDC motor. In other embodiments, depths of about 80–1,000 ft or more can be sampled. The deeper sampling system may be configured with to operate with about 40 in-lbs of torque at about 12.0 rpm, operating with about $\frac{1}{90}$ HP on a 12 VDC motor.

In certain embodiments, the sampling can occur about every 2–6 hours. For low torque systems, a low voltage power source may be used. For larger torque systems additional power may be needed. In certain embodiments, the low voltage power source has a sufficient life to power the system for at least 30 days as will be described further below. "Continuous" means that the automated water profiler can substantially continuously operate at selected intervals over a period of interest such as at least about 1 week, and more typically for about at least 1 month. In certain embodiments, the automated system can operate with little maintenance for about 1 month or longer. The sampling interval can be self-adjusted or adjusted remotely during the monitoring period. For example, upon a detection of abnormal conditions (weather or water parameters), the sampling interval may be automatically increased (based on predetermined criteria defined in a computer program) to obtain additional data, while in periods of relatively constant conditions, the sampling period may be extended.

The system 10 can be configured to obtain measurement readings at desired incremental distances. In certain embodiments, the readings can be obtained every 0.1–5 m, typically at about every 0.5–1.5 m, and more typically at about every 0.5–1 m. The measurement depth intervals may vary depending on the depth of the body of water under analysis as well as the parameters and resolution desired. In addition, different measurement intervals along the water column may be employed to provide increased resolution at depths of particular interest. The automated water profiler system 10 can be configured to obtain the readings from the bottom to the surface (as the probe 35 is raised and the winch 32 winds the cable 33) or from the surface to the bottom (as the probe 35 is lowered and the winch 32 unwinds the cable 33).

Figure 6:
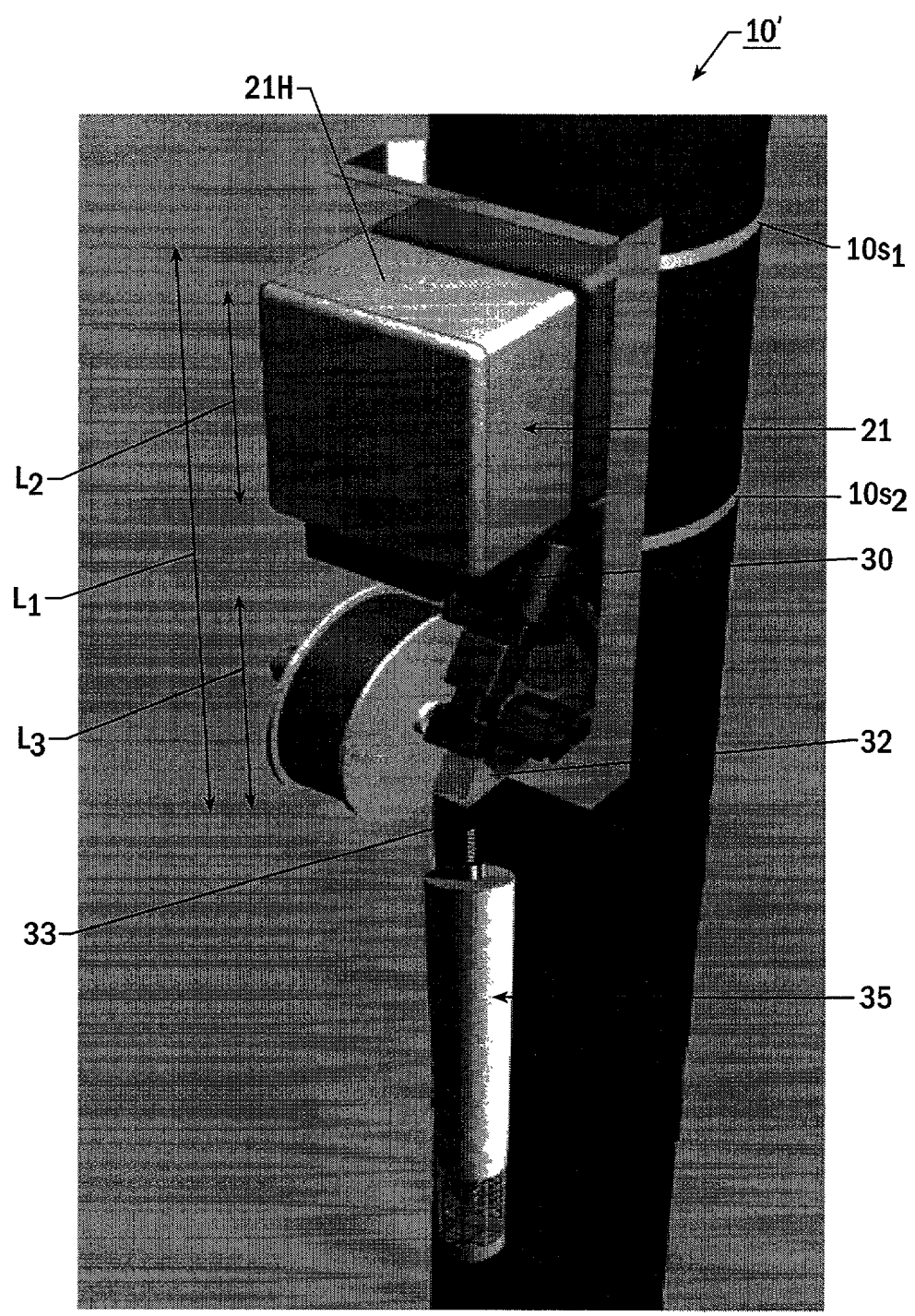
FIG. 6 is a perspective view of a pole mounted profiler system according to embodiments of the present invention.
Figure 7:
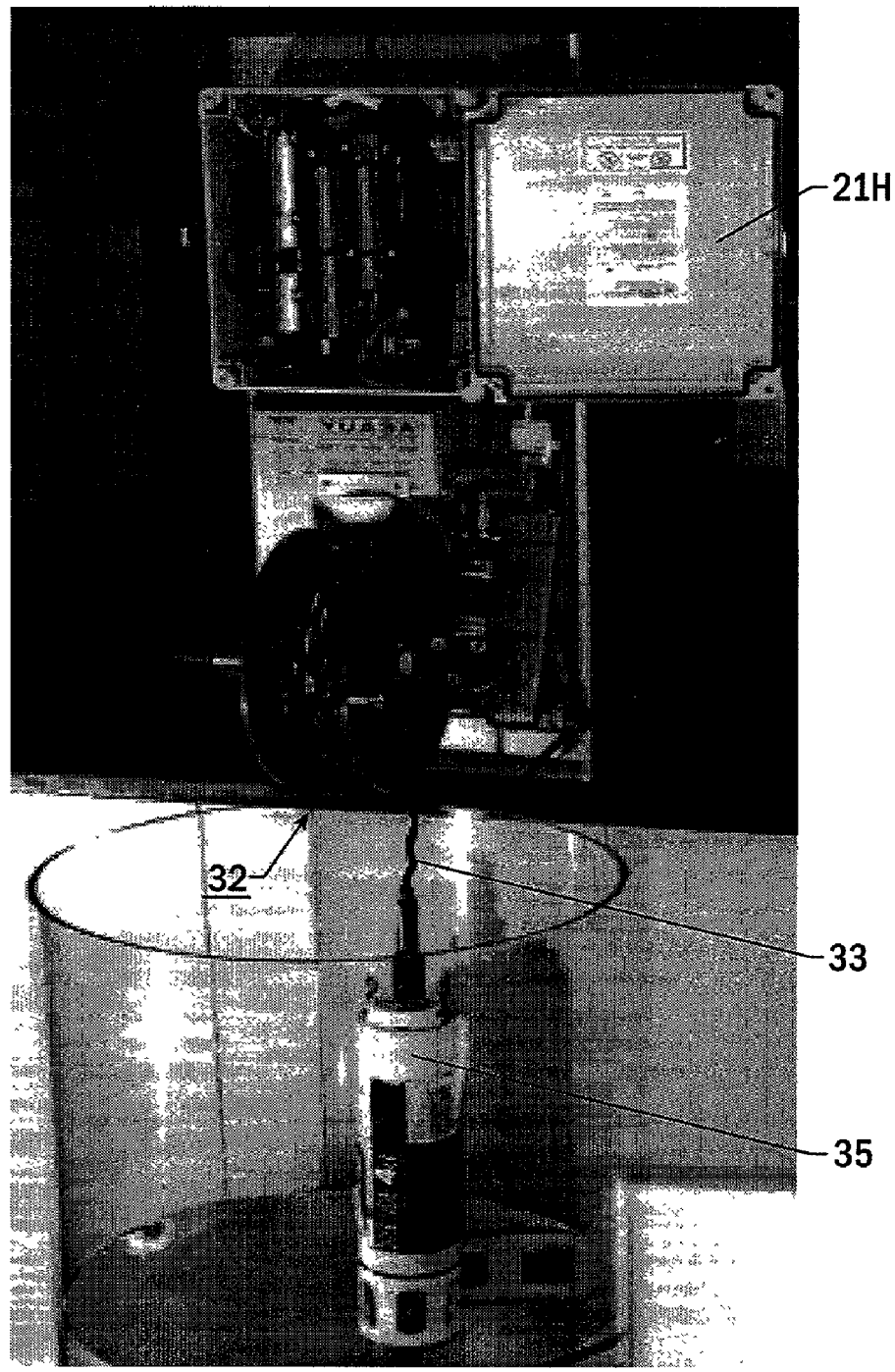
FIG. 7 is a front view of an automated profiler system with the door to a sealable housing holding the electronics thereof, shown in an open position.

As shown in FIG. 6, the power source can be a battery 30 that may be rechargeable via solar energy transmitted from the solar panel (19, FIGS. 1A and 1B). The battery 30 may be a 12V rechargeable battery that is mounted to be relatively easily accessible (externally) to allow ease or replacement during use. As also shown in FIG. 6, the system 10' may be compactly configured as a modular assembly that can be mounted to the side of a piling. The electronics and operational equipment (such as the computer 21, datalogger 121, FIG. 8, communication means such as a cell phone modem 21T, FIG. 8, and electronic relays 13, FIG. 8) can be disposed in a weather resistant protective housing 21H such as NEMA 4X box. FIG. 7 also illustrates one arrangement of the compact modular system 10' (with the door to the housing 21H open). In certain embodiments, the logic-controlled winch 32 can be located below the electronics housing 21H and battery 30.

The modular assembly 10' may be such that the length of the housing of the electronics, shown as $L_2$, may be less than about 12 inches, with the winching spool having a diameter that is also less than about 12 inches, and the total length of the modular assembly $L_1$, covering less than about 24 inches (excluding the probe 35 and cable 33 when unwound). The system 10' can be relatively lightweight, compact, and mountable to the piling with a plurality of banding strips 10s₁, 10s₂ (shown as two). Other mounting configurations and structures may also be used, such as, but not limited to, nails, screws, adhesives, brackets, and the like. In certain embodiments, the modular system 10' (excluding the probe 33) can weigh less than about 50 lbs, and typically less than about 25 lbs.

In certain embodiments, the system 10 is operated to prolong the useful life of the hydrological probe 35 by storing the probe such that it is held submerged or immersed at the bottom of the water column or a depth sufficient to inhibit marine fouling during periods of inactivity. Because the oxygen or DO level (or other potential probe-life reducing agents) is present in reduced amounts at the benthic boundary layer (the layer immediately above the sediment surface) on the order of at least about 0.1 mg/liter dissolved oxygen. The service life can be significantly increased to at least about 9 days compared to 3 days when held in well-oxygenated water. That is, conventionally the oxygen sensor may need servicing at about every 3 days-1 week (i.e., such as changing the membrane), by storing the probe 35 at submerged depth according to embodiments of the present invention, the sensitivity and/or life of the oxygen sensor may be increased. Examples of suitable hydrological probes 35 include multi-sensor probes available from HydroLab Corporation located in Austin, Tex., and other sources such as YSI, Inc., Yellow Springs, Ohio, Sea-Bird, Inc., Bellevue, Wash., Wet Labs, Inc., Philomath, Oreg., Li-Cor, Inc., Lincoln, Nebr., and Turner Designs, Inc., Sunnyvale, Calif., and the like. Other examples of hydrological probes are discussed in U.S. Pat. Nos. 5,816,874, 5,821,405, and 4,662,210; the contents of these documents are hereby incorporated by reference as if recited in full herein. The multi-sensor integrated hydrological probe 35 can be configured with one or more of a depth sensor, a dissolved oxygen sensor, a turbidity sensor, a salinity sensor, a pH sensor, a temperature sensor, a chlorophyll sensor, a conductivity sensor and the like.

The right side of FIG. 2A illustrates examples of visual and graphic displays of water profile data and associated meteorological data which can be gathered by automated water profiler systems 10, 10' and charted or monitored over time to generate dynamic information of evolving conditions. The five lower graphs track a five-day period and depict the variation in water level, specific conductivity, DO percentage, redox, and pH at Broad Creek. The upper graphs illustrate wind speed/direction and barometric pressure and air temperature with relative humidity and rainfall (hourly) measured at Kennel Beach over the same five-day period. The graphic depiction of gauges at the top of FIG. 2A, illustrates the meteorological conditions at Carolina Pines at a particular date and time (Dec. 11, 2000 at 5:00 PM). In FIG. 2A, DO % (mg/L), air temperature (C/F), wind speed (mph, m/s and knots), wind direction, voltage, water sample depth, bar pressure, and water temperature are shown. These displays can be generated by a data acquisition computer that may be located at a central collection site (typically shore-based) and uploaded to be displayed on a global computer network at a desired website URL which is accessible by interested persons. The data may be transmitted from the different monitoring sites to the data acquisition computer using substantially real-time data, allowing the displays to be updated in substantially real time (such as from about 1–30 minutes or less from transmission from the monitored site) and posted to a desired user accessible site or sites.

Figure 2B:
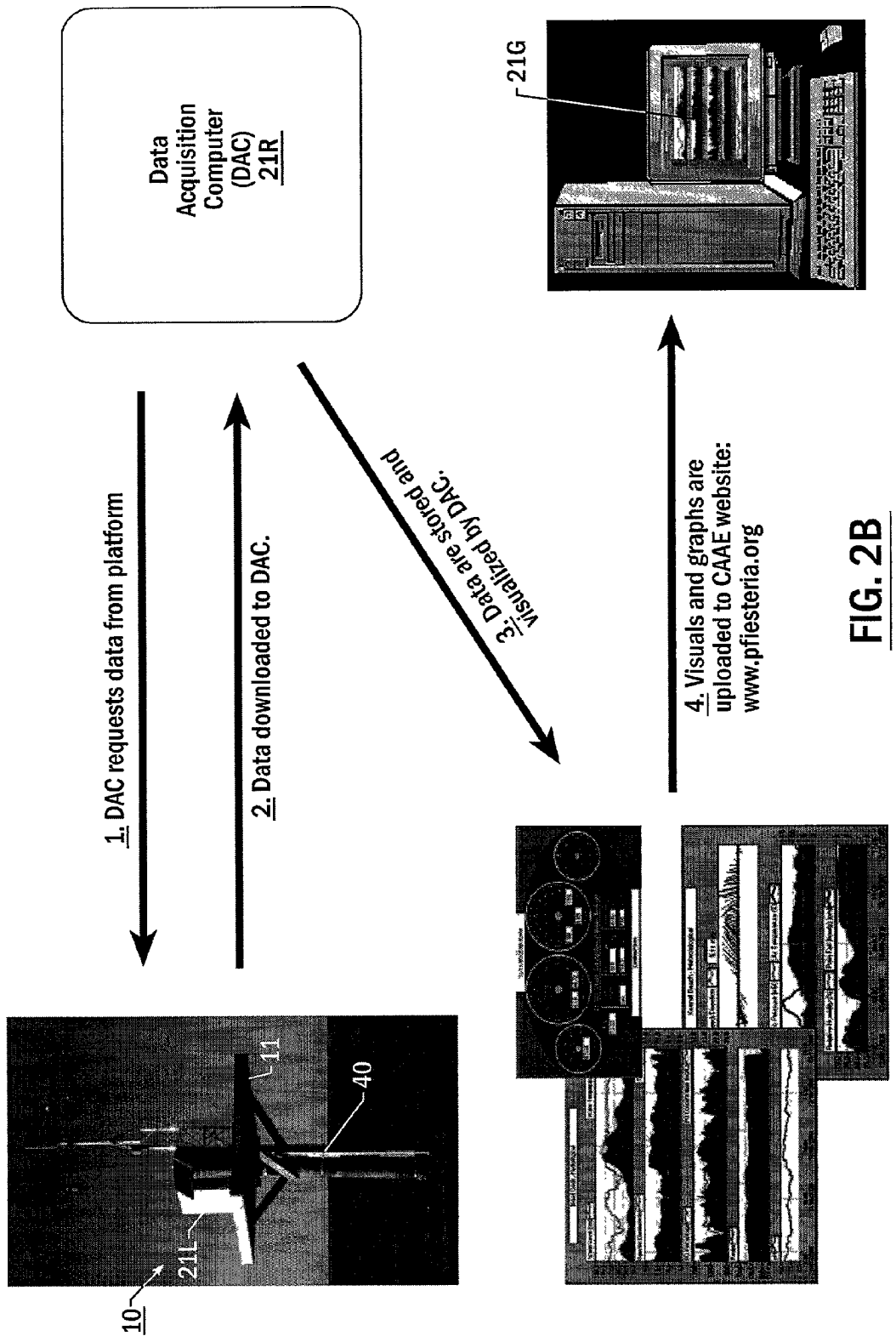
FIG. 2B is a schematic illustration of a water profiler data acquisition, evaluation, and presentation system providing screen displays of monitored parameters according to embodiments of the present invention.

FIG. 2B is a screen printout of operations that can be performed for a data collection system according to certain embodiments of the present invention. As shown, a remote data acquisition computer 21R (located remote from the local computer 21L at the profiler 10, 10') can wirelessly communicate with the local computer 21L to request data transmission from at least one local system 10, 10'. In response, the local computer 21L, at the profiler system 10, 10' transmits the data to the remote computer 21R. This data is analyzed and graphics generated to illustrate the monitored dynamic parameters over a desired time period as shown by the graphs and meter visuals in the lower left corner of FIG. 2B. This data and graphic information can be transmitted to a global computer network 21G that may be accessed (shown as located at URL www.pfiesteria.org). In certain embodiments, email alerts can be generated and sent to list serve individuals (or those wishing to be given such notice) when unusual conditions are detected allowing a user to more closely monitor those situations.

Figure 2C:
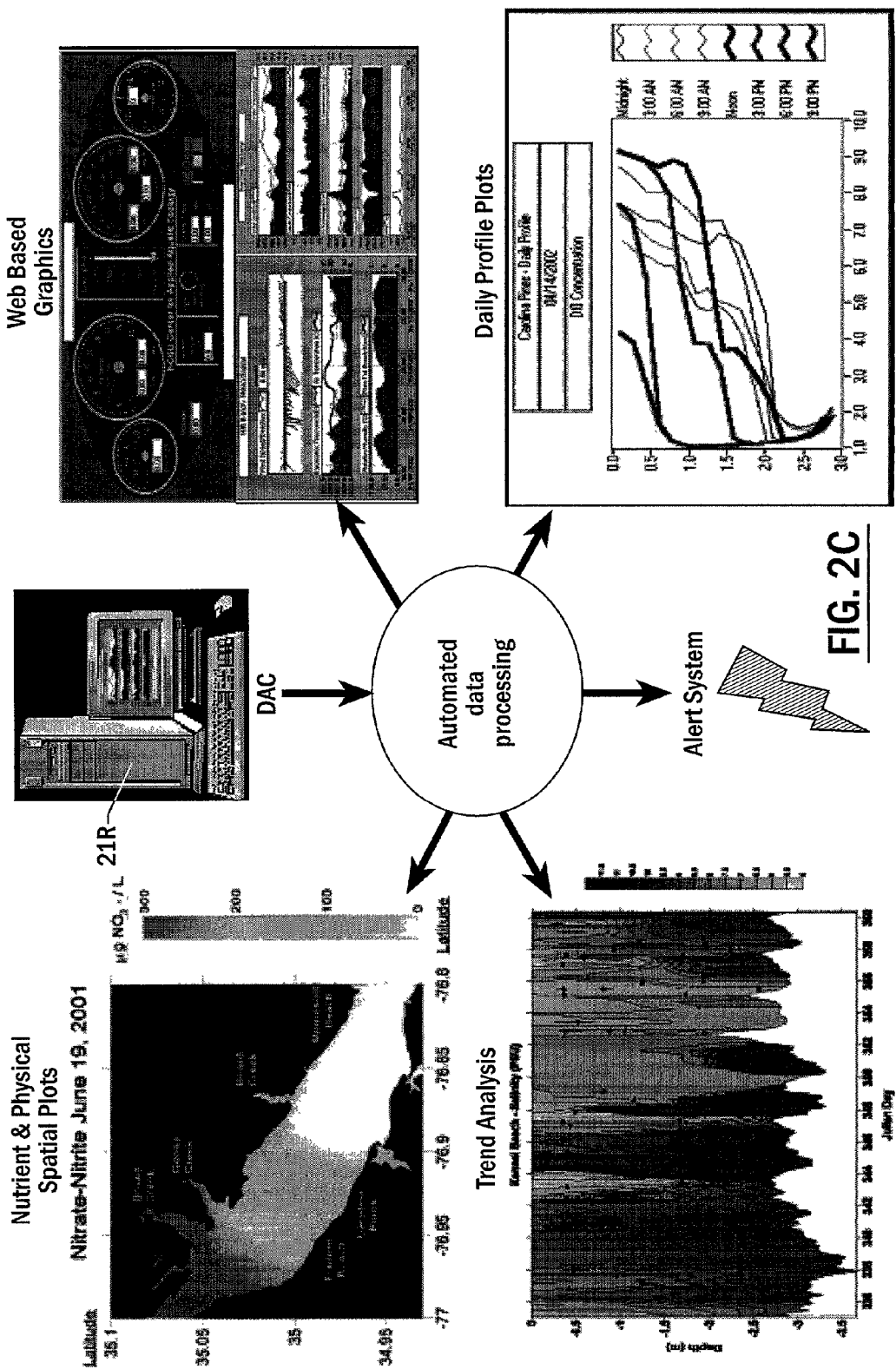
FIG. 2C is a schematic illustration of an automated data processing system that acquires, evaluates and presents data and generates alerts according to embodiments of the present invention.

FIG. 2C is a screen print out that illustrates examples of graphic presentations and/or analysis that may be performed of the data according to embodiments of the present invention. The graphics and analysis may include, but is not limited to, nutrient and physical spatial plots, trend analysis, regionally or at desired locations, daily profile reports, and wind, rain, and other graphic data associated with environmental conditions at the time of the data collection. The graphs may be presented in gray scale or color.

Figure 3:
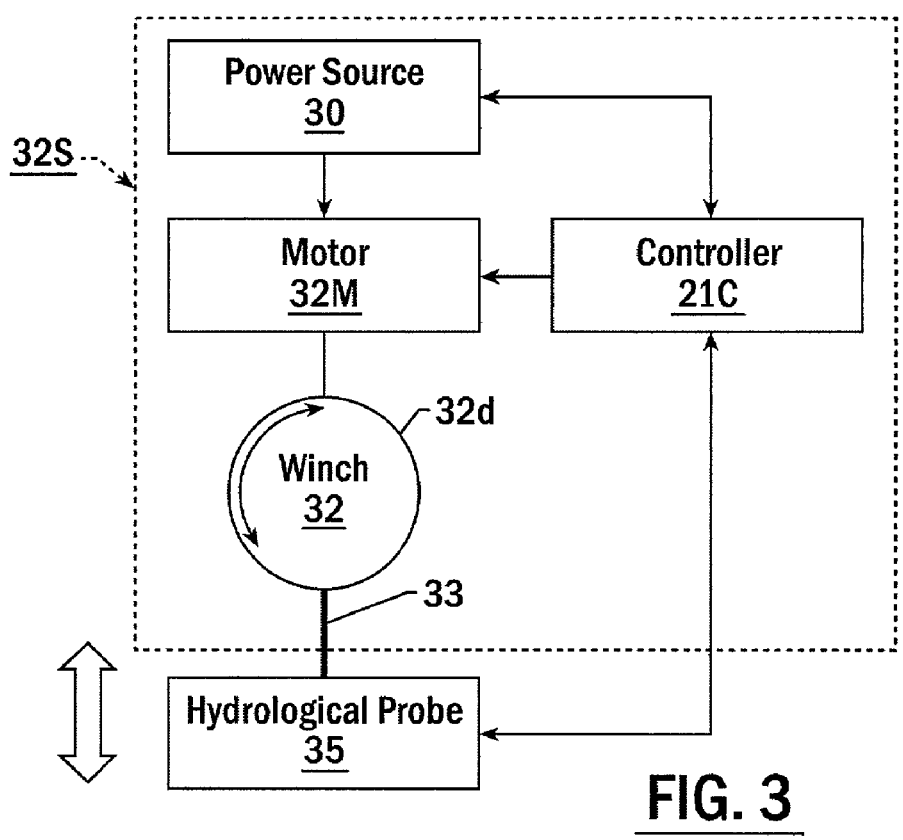
FIG. 3 is a schematic illustration of a hydrological probe and winch according to embodiments of the present invention.

Turning now to FIG. 3, one embodiment of a relatively low cost winching system 32S for selectively winding and unwinding the cable thereby raising and lowering the probe 35 is illustrated. As shown, the winching system 32S includes a power source 30, a controller 21C, a motor 32M, and a winch 32 which includes the cable drum assembly or spool 32d. A desired amount of cable 33 is wrapped onto the cable drum assembly. An example of a suitable cable is an eight conductor electro-mechanical cable from Hydrolab, Inc. of Austin, Tex. The motor 32M can be configured so as to be suitably powered by a power source 30. In certain embodiments, the motor 32M can operate based on power supplied by one or more batteries having a service life of at least about 30 days when sampled at the desired sampling interval(s) noted above. An example of a suitable motor is the Dayton 12V electric motor, which has a 0.45 rpm rating, and associated gearhead from Grainger Industrial Supply of Raleigh, N.C., as part no. 4Z832.

In certain embodiments, the power source 30 is low voltage DC power source having a voltage of about 24V or less. In certain embodiments, a single 12V marine battery will suffice. An example of a suitable battery is a general purpose, deep cycle marine battery from Boaters World in Raleigh, N.C. The cable assembly drum 32d can be configured with a sufficient width and depth to hold the desired length of cable. The drum 32d can be fabricated from a corrosion resistant material having sufficient material strength to hold the cable 33. In certain embodiments, the drum 32d can be made from readily available and inexpensive sheet PVC (polyvinylchloride) plastic and schedule 40 plastic or elastomeric PVC pipe. The diameter of the spool 32d is sufficient to provide an adequate bending radius for the electromechanical cable wrapped thereon. In certain embodiments, the spool diameter is about 3 inches or greater. The number of revolutions per minute that the drum or spool 32d operates at can be dependent upon the choice of the drive motor, the related gearing, and the like, as is known to those of skill in the art.

The controller 21C can be a central controller or a supplemental controller in communication with the main controller. The main or primary controller can be located at a platform and/or at one or more remote sites (whether a central facility or a primary platform station). The controller 21C can be a computer (such as a laptop or a pervasive wireless computer device) and/or a digital signal processor that is able to receive wireless transmissions and obtain and transmit desired data from and to one or more remote sites. The controller 21C can include a CR10X datalogger from Campbell Scientific of Logan, Utah.

Figure 4:
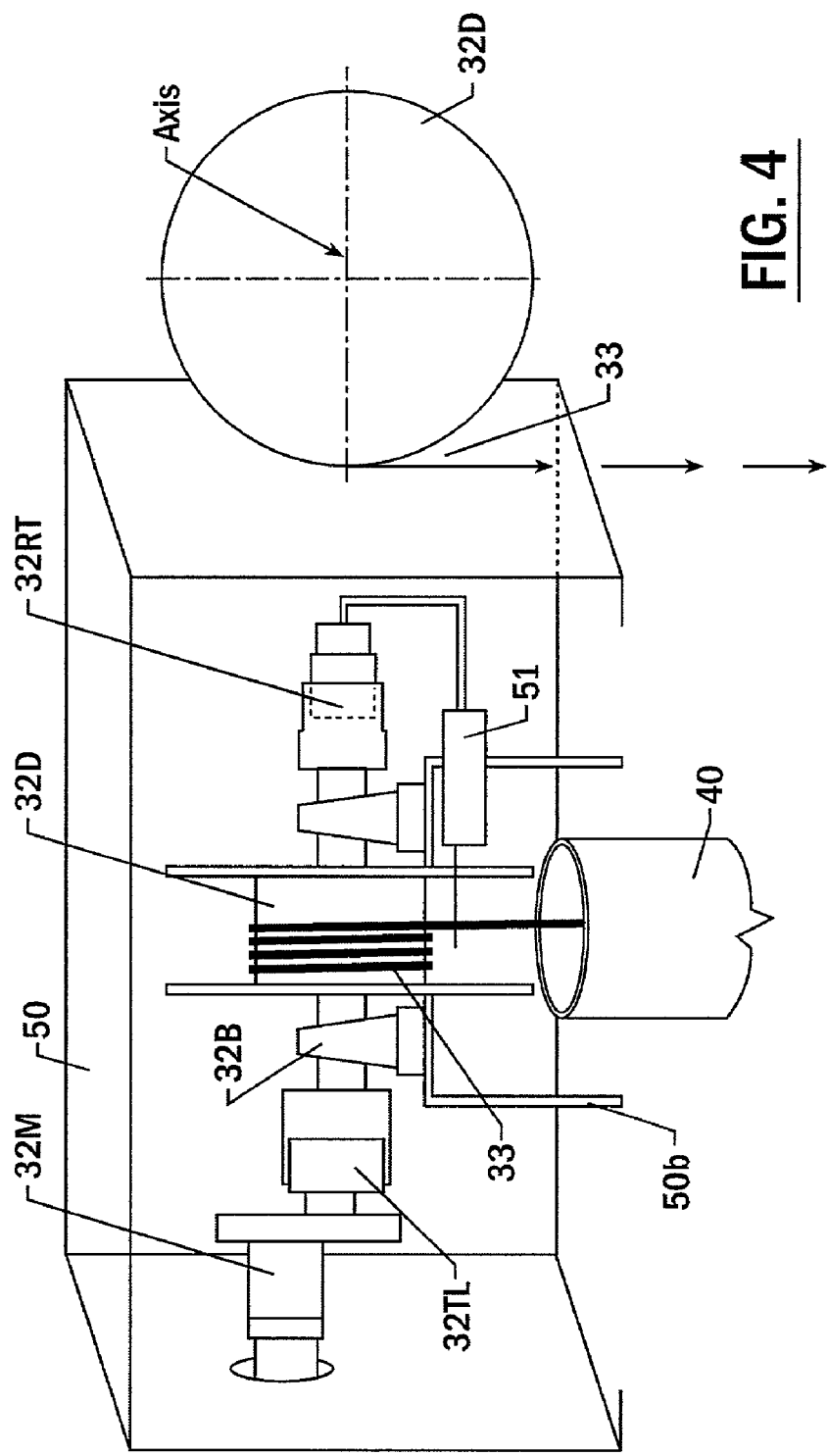
FIG. 4 is a front view of a winching system according to embodiments of the present invention.

FIG. 4 illustrates an embodiment of a winching system 32S. As shown, in cutaway view (with the housing 50 partially removed), the winching system (or at least the winch 32 and drum 32d, spooled cable 33, and motor 32M) is enclosed in a housing to protect the equipment from the environment. The drum 32d can be held suspended or mounted above the platform or guide tube 40 (where used) by a bracket 50b which can be attached to the floor or ceiling (or side walls) of the housing 50. In other embodiments, the bracket 50b can mount directly to the platform itself.

Figure 5:
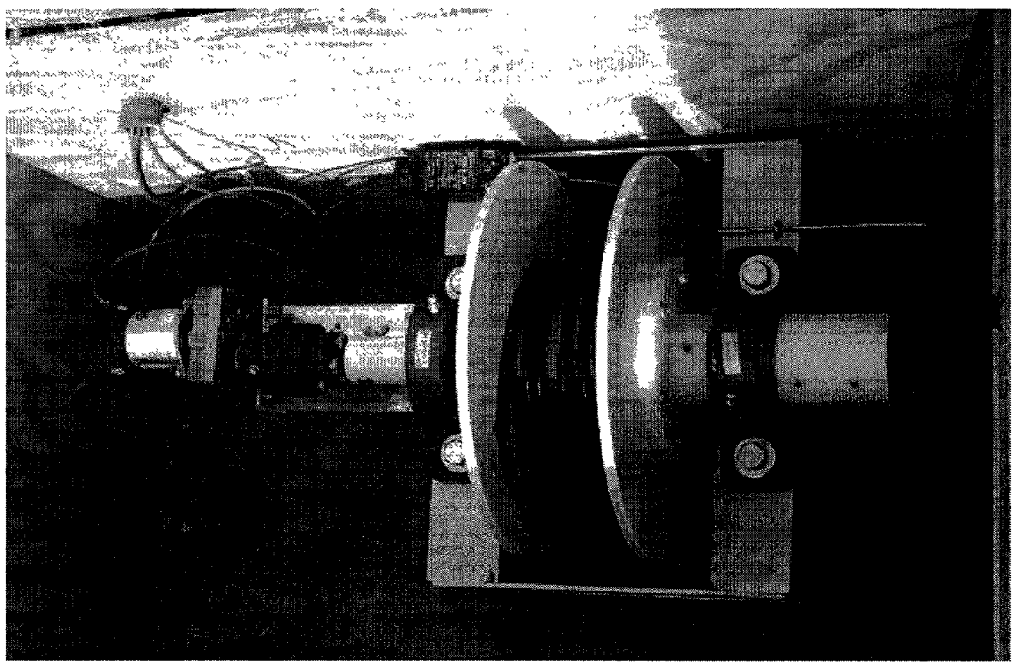
FIG. 5 is a digital photograph of a winching system according to embodiments of the present invention.

As shown, the winching system 32S can include other components including a multi-conductor rotating connector 32RT such as an eight conductor Mercotac 830-SS E00 available from Mercotack, Inc. or Carlsbad, Calif., a torque limiter 32TL such as a Zero-max/Helland model H-T.L.C., available from Small Parts, Inc. of Miami, Fla., a limit switch 51 such as a Telemecanique limit switch (single pole, double throw, omnidirectional) part no. XCKP 106 available from Grainger Industrial Supply, of Raleigh, N.C., and bearings 32B. The rotating connector 32RT may be configured as a relatively low cost connector with mercury contacts. The motor 32M may be operably associated with a 90 degree gearbox as is known to those of skill in the art and other wiring and circuitry may be used to provide the communications and signal path(s). For example, a solid-state relay (such as a Crydom D1D07 MOSFET solid relay from Newark Electronics of Greensboro, N.C.) may be positioned operably between the winch motor 32M and the datalogger or signal processor (not shown). FIG. 5 is a screen printout of an economical winching system illustrative of that shown in FIG. 4.

The drum 32d can be aligned with the line of cable 33 movement into the water or can be laterally offset from the line of movement so that the cable 33 travels through an angle before it turns and vertically travels in the water column. FIG. 2A illustrates that, in certain embodiments, the drum 32d is spaced away from the vertical line of travel and the cable 33 first travels out from the drum 32d at an angle of about 30–60 degrees for a distance and then turns so that it is vertically oriented as it enters the water. FIG. 4 illustrates that the cable/winch 32d is vertically aligned so that the cable 33 is released from the spool/drum 32d in a substantially vertical line. The drum 32d can be positioned over and vertically aligned with the aperture in the platform/guide tube.

Figure 8:
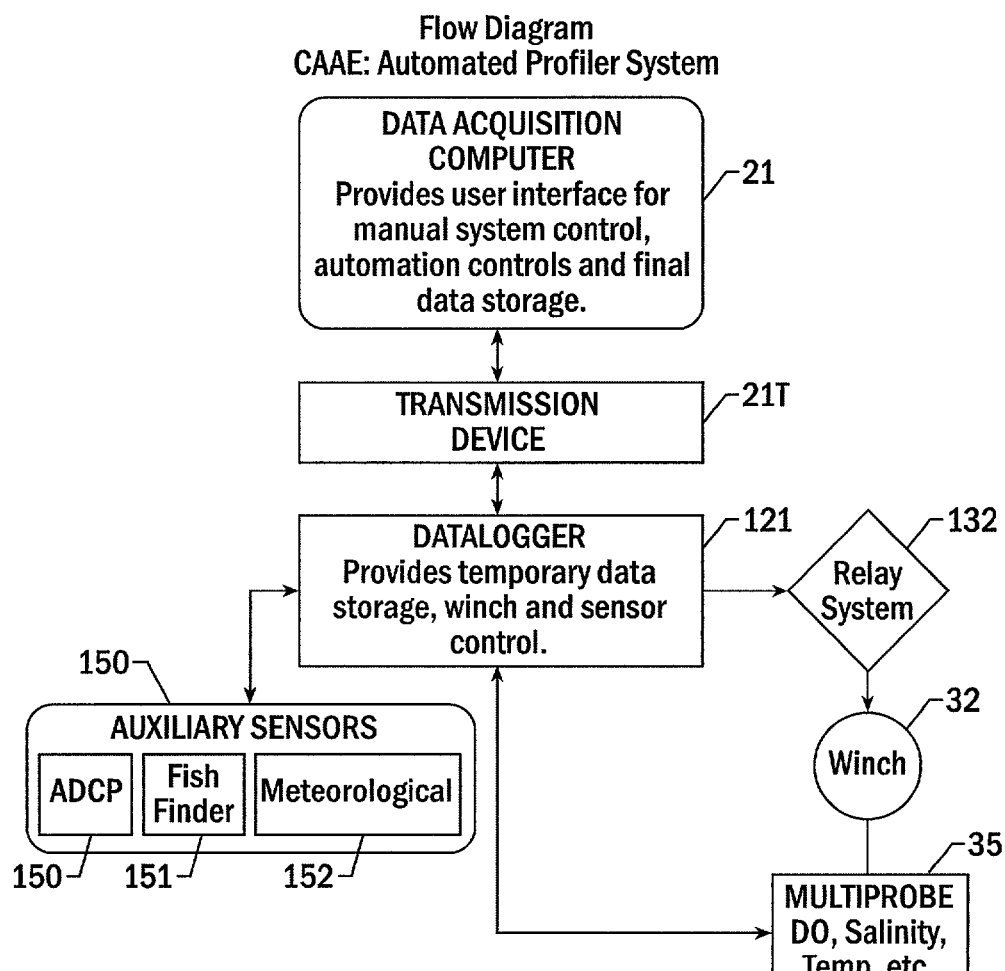
FIG. 8 is a schematic illustration of an automated profiler system according to embodiments of the present invention.

FIG. 8 is a schematic illustration of the automated profiler system 10 according to embodiments of the present invention. As shown, the system 10 includes a data acquisition computer 21 and a datalogger 121. The computer 21 and datalogger 121 are in communication via a transmission device 21T. The datalogger 121 may be a module on the computer 21, or a separate computer, controller, or signal processor. The computer 21 can be configured to allow user interface for manual system control (via input delivered on site or from a remote site) and includes the automated program operations and data storage. The datalogger 121 provides temporary data storage and winch and/or sensor control. The computer 21 and datalogger 121 can control the operation of the winch 32 and probe 35 via a relay system 132. The measurement data or signals from the probe 35 can be directed to the datalogger 121. The datalogger 121 may also operate and receive data from auxiliary sensors 150 which can include a fish finder (sonar) sensor 151, meteorological sensors 152, and an ADCP (Acoustic Doppler Current Profiler) sensor.

In certain embodiments, the system 10 can include other communication components such as a cell phone, a voice synthesizer and/or modem, such as a COM300 voice synthesizer and modem from Campbell Scientific of Logan, Utah.

Figure 9:
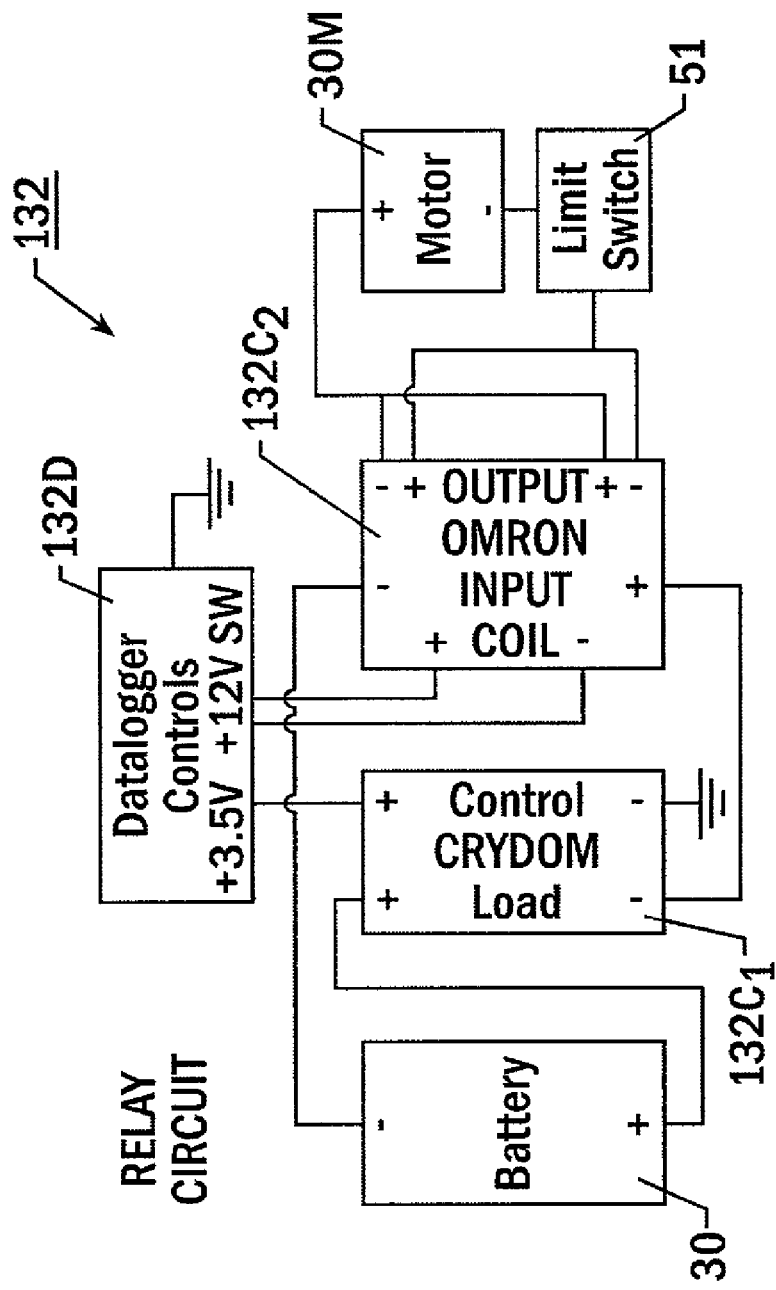
FIG. 9 is a schematic illustration of an exemplary relay circuit suitable for the relay system shown in FIG. 8.

FIG. 9 illustrates an example of a relay circuit or system 132 (FIG. 8) used to control the winding and unwinding of the winch or coil 32. As shown, the relay circuit 132 includes datalogger controls 132D that communicate with a CRYDOM load control component $132C_1$, and a coil OMRON output component $132C_2$. The relay system 132 can also include a limit switch 51, battery 30, and the motor 30M. The CRYDOM relay is available from Crydom Corporation, located in San Diego, Calif. The OMRON coil output component is available from Omron Electronics, LLC, located in Schaumburg, Ill.

Figure 10:
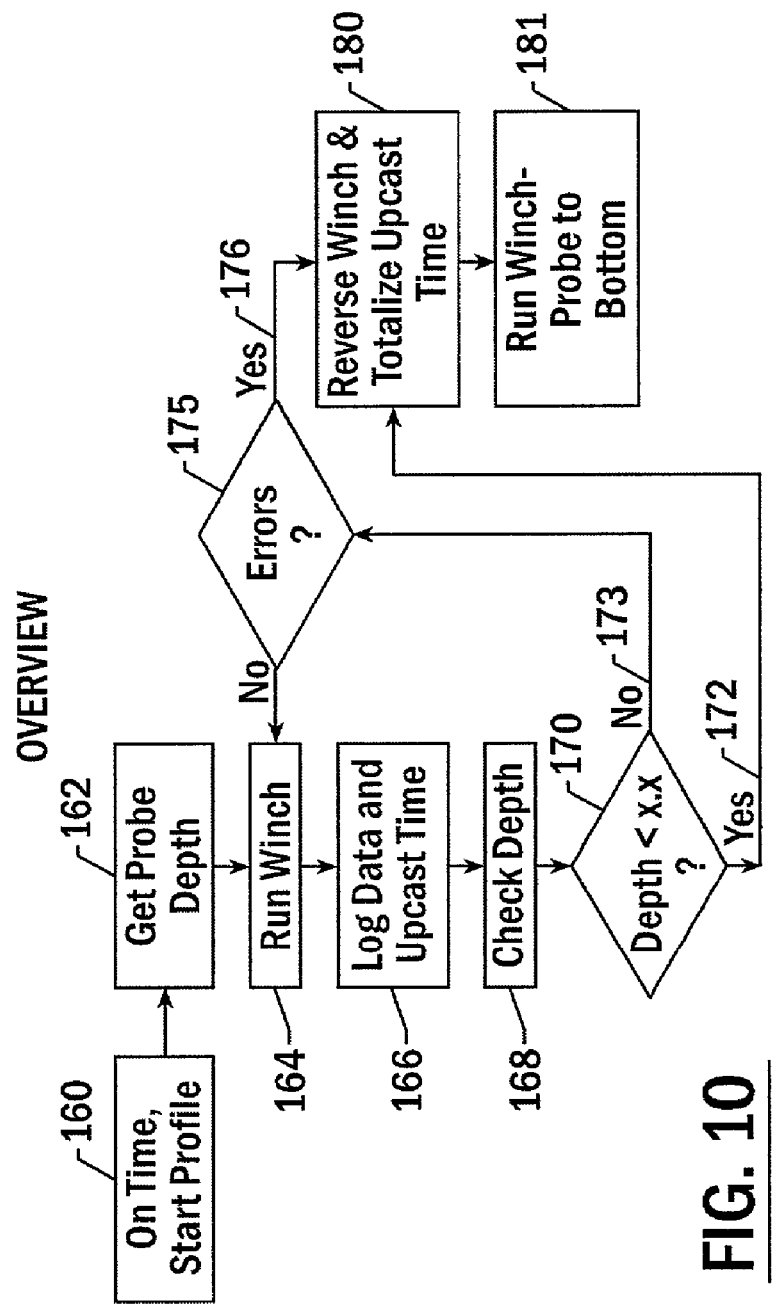
FIG. 10 is a flow chart of an example of logic control operations that may be performed according to embodiments of the present invention.
Figure 11:
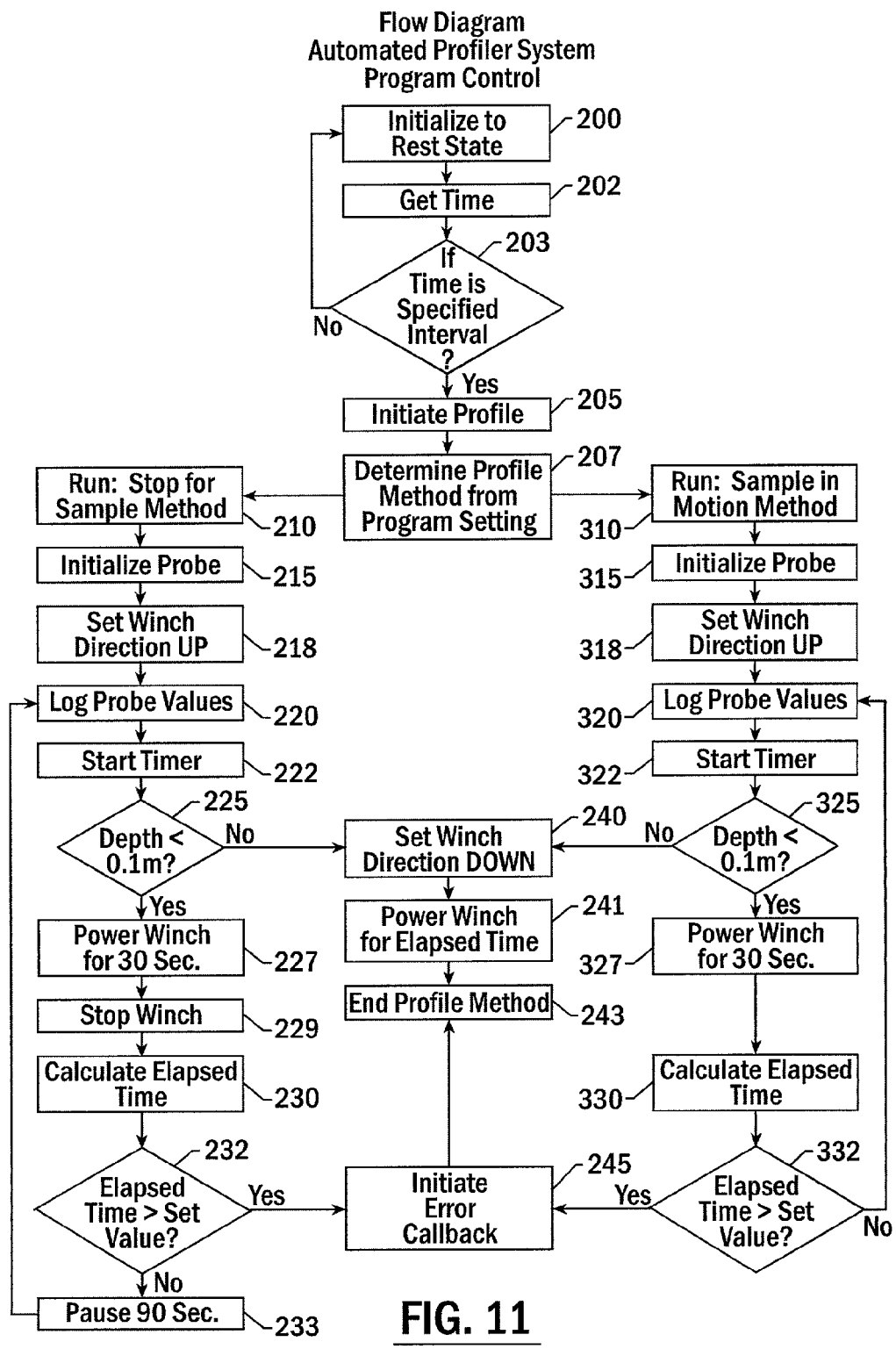
FIG. 11 is a flow chart of operations of an automated profiler system according to embodiments of the present invention.

Examples of operations that can be used to obtain dynamic water profile data are shown in FIGS. 10 and 11. FIG. 10 illustrates an example of operations that may be carried out in a logic control data loop according to certain embodiments of the present invention. At a designated or desired time, the profile is initiated (block 160) and the probe depth is determined (block 162). The winch 10 is powered and run (block 164). The data is collected and logged along with the upcast time (block 166). The depth is evaluated (block 168). A decision box (block 170) evaluates whether the depth is off by more than a desired amount from a predicted value. If the depth is within the predetermined tolerance (yes, block 172), the winch movement is reversed and the upcast time is totalized (block 180). The probe is then winched to the bottom (block 181).

If the depth varies beyond the predetermined amount (no, block 173) an error identification routine (self-diagnostic program) may be performed to identify whether there is an error in the procedures or collection routine (block 175). If an error is identified, certain operations repeated (shown as blocks 164, 166, 168, and 170).

Referring to FIG. 11, in certain embodiments, operations include initializing a rest state (block 200). The time is obtained (block 202) and it is determined whether the time is at a specified interval (block 203). If the time is not at a specified interval, the operational sequence returns to the initialized rest state (block 200). If the time is at a specified interval then the profile sequence is initiated (block 205). The desired profile method is determined from the default or altered (updated) instructions (block 207) to proceed either in a run mode which samples pausing the probe so that the probe will dwell at certain depths (block 210) or to sample in motion (block 310). The sample in motion method may selectively employ slower descent or ascent times during the profiling period or can be run at a constant rate.

For the stop for sample operational sequence (block 210), the probe can be initialized (block 215), and the winch set to wind in a desired direction. As shown, the winch is set to wind up (block 218) to raise the probe. This is because, in certain embodiments, the probe start position can be at the bottom of the water column as noted above. In other embodiments, the sequence for the probe movement and/or sampling measurements for both the motion and stop sample methods can start from a winch direction down to take measurements as the probe descends.

The probe can obtain the measurements and the data or probe values can be logged or stored (block 220). The timer can be started (block 222). At certain depth intervals, depth measurements are obtained and it is determined as to whether the depth is less than about 0.1 m (block 225). If yes, then the winch is powered for a desired time, shown as about 30 seconds (block 227) and the winch is stopped (block 229) and the elapsed time calculated (block 230). The operation determines whether the elapsed time is greater than a predetermined set value (block 232). If not, then the probe is paused so that it dwells at that depth for a desired time (shown as about 90 seconds) (block 233) only to log the measured values (block 220), and the sequence is repeated for an incremental depth. If the depth was determined to be less than about 0.1 m, then the winch can be redirected to a down direction (block 240) and the winch powered for an elapsed time (block 241) so that the probe travels to the desired storage location. The profile method can be terminated (block 243). If the elapsed time is greater than the set time (block 232) during the upward sequence, a safety initiate error callback operation can be run (block 245).

The "sample in motion" method (block 310) can include similar operations. That is, the probe can be initialized (block 315), and the winch set in an upward direction (block 318). The probe values can be stored or logged (block 320) and the timer started (block 322). The probe depth can be measured to assess whether it is approaching the surface (shown as determining whether the depth is less than about 0.1 m) (block 325). If the answer is yes, the winch is set to move in the downward direction (block 240), the power to the winch is activated for an elapsed desired time (block 241) to position the probe at its inactive location, and the profile sampling is terminated (block 243).

In certain embodiments, those operations associated with blocks 325, 225, can be performed such that the datalogger automatically communicates with a serial data interface (such as a SDI-12 or serial data interface 1200 baud as described at http: sdi-12.org) which is operably associated with the probe to record the probe/SDI-12 depth. This depth value can be used as an input into the datalogger program for the conditional yes/no decision. Motor control (i.e., powering of the winch) can be performed via the execution of software commands which can be made dependent upon the conditional response. For example, if the sensor depth is greater than 0.1 m, then the motor can continue in an upcast mode. If the depth is less than about 0.1 m, then the motor can be reversed and the sensor moved to the bottom of the water column, as desired. The particular decision depth can be adjusted to be less (or more) than the 0.1 m depending on the location of the depth sensor relative to the probe sensors and/or depending on whether an adjustable surface level measurement is desired. For example, but not limited to, the directional decision depth may be defined as between about 0.05 m–0.2 m.

Thus, if the probe depth is greater than about 0.1 m, then the winch is powered for a desired time (shown as 30 seconds)(block 327) and the elapsed time is calculated (block 330). The elapsed time is evaluated to determine whether it is above a set value (block 332). If the elapsed time is greater than a set value, then the error callback sequence is initiated (block 245). If the elapsed time is less than the set time, the probe values are logged and the sequence run to repeat the operations (blocks 320, 322, 325, 327, and 330).

In addition, the system can be configured to detect, alert, and correct certain operational features. For example, in certain embodiments, the system can be programmed to self-correct or reset the probe depth or location when sensors or switches (such as limit switches) indicate it is not at a proper level. The improper depth may occur because the line is caught or the probe is hung up or wedged against the side of the guide. In other embodiments, the system can include program code and sensors that activate remote alarms when certain predetermined conditions are identified, allowing a monitoring station to undertake to remedy the detected condition in a manner that reduces any corrupted data that may be attributed to the predetermined conditions. Examples of such predetermined conditions include, irregular water conditions which depart by more than a predicted limit from a norm, high winds, high seas, low power, the inability to winch up or down, and the like.

In certain embodiments, the datalogger can initiate a telephone call when selected parameters are over or under the desired or a predetermined range. The selected parameters can include at least one of: DO (dissolved oxygen), profiler depth, detected battery upcast loop error in the handling of the probe (typically for when or if the profiler stalls for any reason on the upcast, the program exits the logic loop and returns the probe to the bottom location. The system can also identify if the probe is not returned to a proper desired resting depth. The winch can be powered again to attempt to lower the probe further. The depth error features can be linked to a depth callback alarm. In other embodiments, a sensor can be used to obtain a vibrating wire depth reading for an optional water level sensor.

In other embodiments, the average DO is calculated and a daily (or other desired report or collection interval) can be generated, from desired input locations and by geographic locations that can be identified by geographic coordinates or other site identifiers. Of course, other data evaluations of the DO data can be used such as range data (highs and/or lows or median values and the like). The geographic coordinates or site identifiers can be included in the data transmissions facilitating input in a system including a plurality of different collection sites for easier analysis in a GIS system.

In certain embodiments, the automated system can be used to monitor water used to raise captive or farm-grown fishes (fisheries) (not shown). For example, the automated system 10 can be operably associated with a containment bed that can enclose a plurality of fishes held captured therein in a body of water. The containment bed can be configured to be able to be moved from one desired location to another. The automated system 10 can be programmed to monitor the conditions proximate the containment beds and then to increase or decrease the depth at which the containment beds are located automatically over a desired period in order to take advantage of improved conditions (suitable oxygenation) or to avoid undesirable conditions (increased numbers of potential toxins). Similarly, the automated systems can be configured to identify the presence of unsuitable swimming conditions and/or to monitor bodies of water for spills, leaks, chemicals, toxins, or other parameters to note and/or track the consequences or reactions of the water to the introduction of substances therein which may indicate a potential environmental impact. In addition, the water or liquid profile data can be used to assess when it may be desirable to introduce (or reduce or stop the introduction of) certain additives, treatments, or substances to the water to counteract unfavorable detected conditions (such as increased blue green algae). In other embodiments, the profiler 10 can be used to track water conditions in shipping lanes in the ocean, as well as water columns adjacent oilrigs and platforms.

As will be appreciated by one of skill in the art, the present invention may be embodied as an apparatus, a method, data or signal processing system, or computer program product. Accordingly, the present invention may take the form of an entirely hardware embodiment, an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as BASIC, Java®, Labview, Smalltalk or C++. However, the computer program code for carrying out operations of the present invention may also be written in conventional procedural programming languages, such as the "C" programming language or even assembly language. The program code may execute entirely on the user's (monitoring site) computer, partly on the user's computer as a stand-alone software package, partly on the user's computer and partly on a remote computer or entirely on the remote computer. In the latter scenario, the remote computer may be connected to the user's computer through wireless means and/or via a local area network (LAN) or a wide area network (WAN), or the connection may be made to an external computer (for example, through the Internet using an Internet Service Provider).

The flowcharts and block diagrams of certain of the figures herein illustrate the architecture, functionality, and operation of possible implementations of water profiling systems and/or probe operation and storage systems according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

The present invention will be explained further by the non-limiting examples described below.

EXAMPLES

Figure 12A:
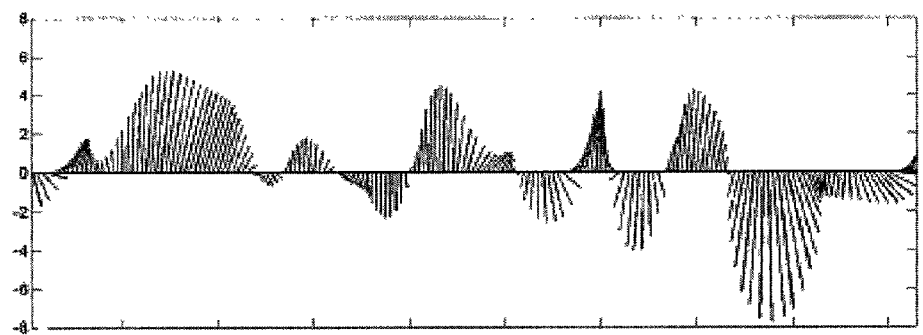
FIGS. 12A–12C are graphs of dynamic water profile data according to embodiments of the present invention.
Figure 12B:
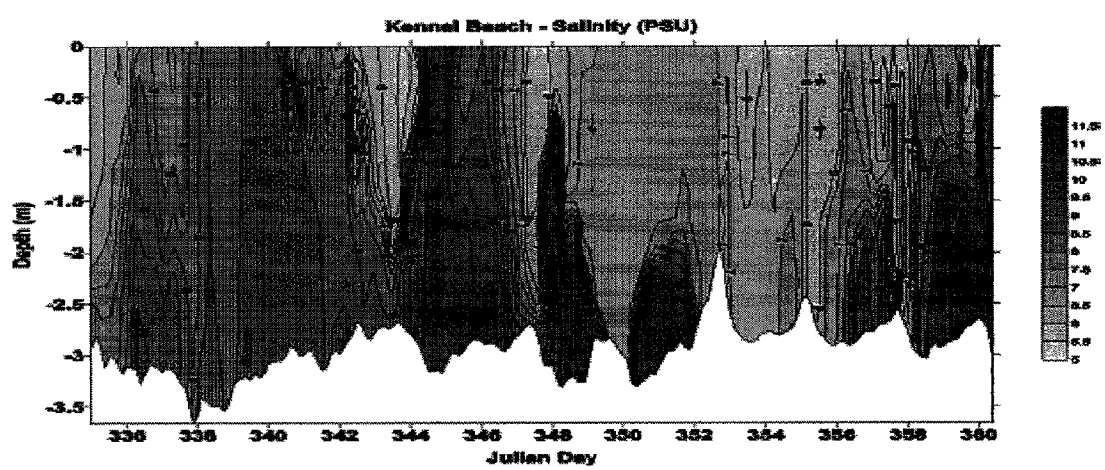
Figure 12C:
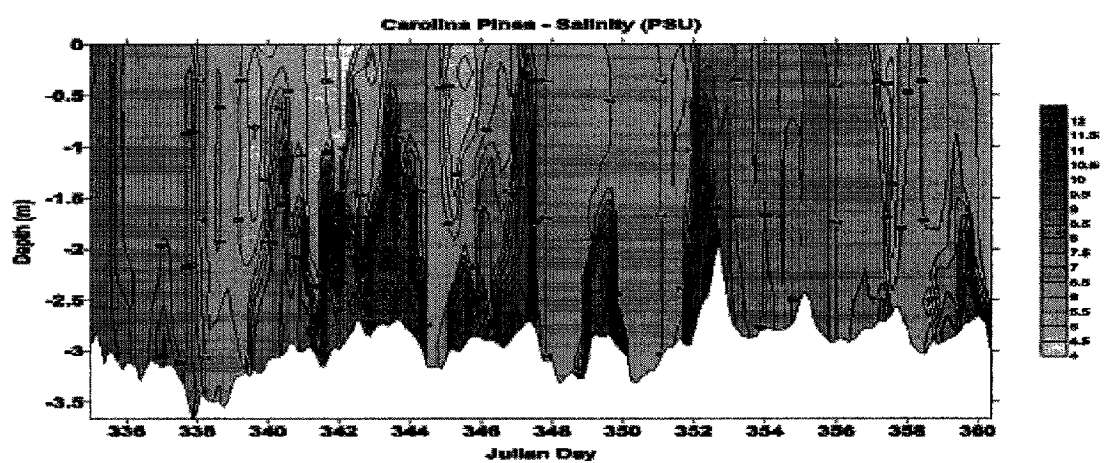

FIGS. 12A–12C are graphs of dynamic water profile data illustrating a water column response to large magnitude wind events of water columns positioned to be exposed to cross-estuary winds, according to embodiments of the present invention. FIG. 12A illustrates the wind conditions (direction and speed) over a selected time period. FIG. 12B illustrates a gray scale of gradient of salinity (PSU) at a first site located at the north shore of Kennel Beach over a corresponding time period (shown in Jullan Day). The side legend defines the levels of salinity corresponding to the gray scale shown. FIG. 12C illustrates similar data for a second site located at the south shore of Carolina Pines. Although shown in gray scale, color gradient graphs can also be used to illustrate the spatial distribution of the measured parameter. As shown, large magnitude wind events promotes a well-mixed water column and large fluctuations in water level (shown by the bottom of the graphs from more than −3.5 m to about −2.0 m). The "0" level shown is for the bottom of the water column shown as the top of the graph. The graphs illustrate that the water profiler is able to provide resolution of subtle salinity differences throughout the water column.

Figure 13A:
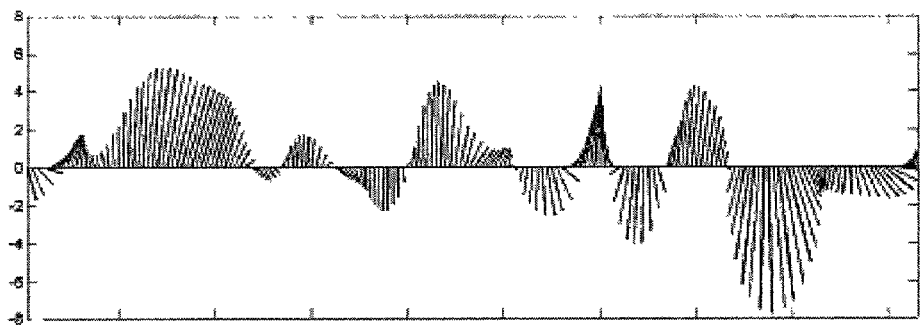
FIGS. 13A–13C are graphs corresponding to the graphs of FIGS. 12A–12C. The wind conditions shown in FIG. 13A are the same as for that in FIG. 12A. In these figures, the sensor detects or measures for the presence of detected DO (dissolved oxygen) in the water column, according to embodiments of the present invention.
Figure 13B:
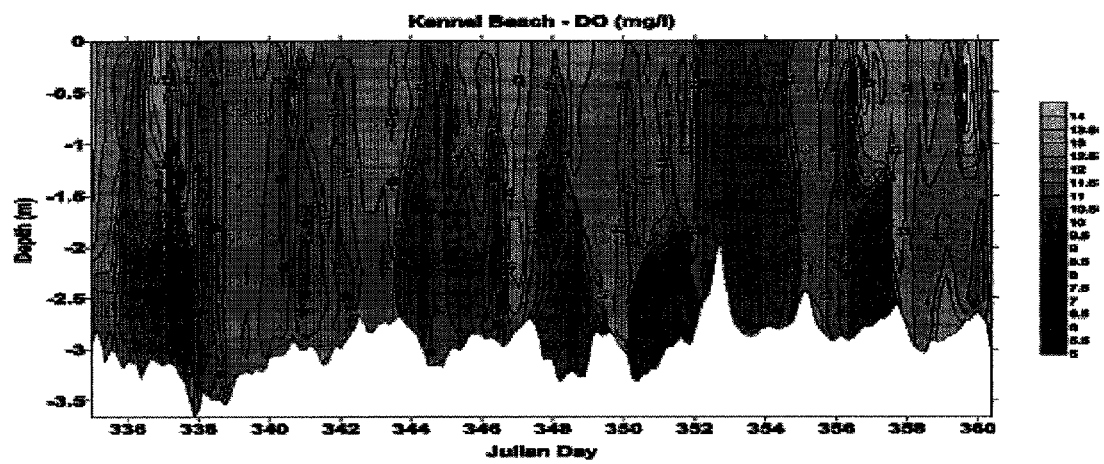
Figure 13C:
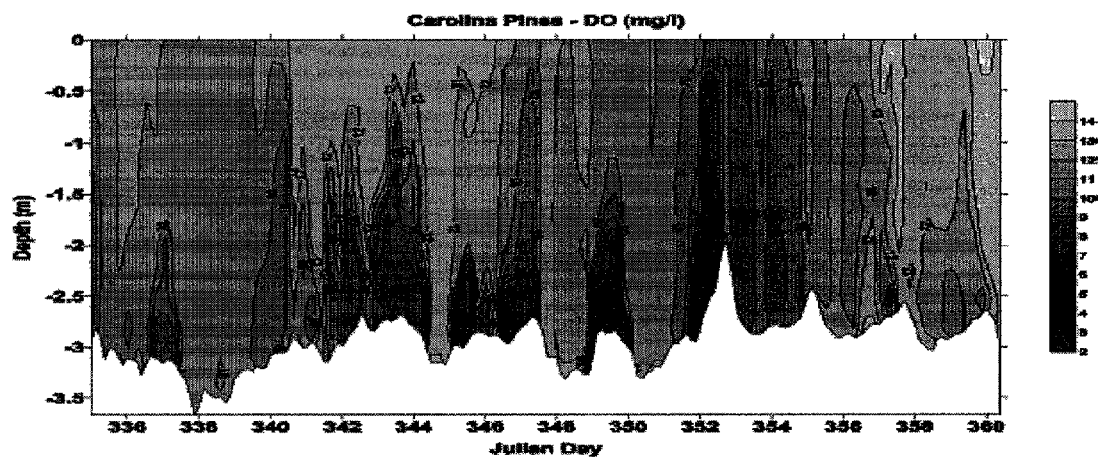

FIGS. 13A–13C are graphs corresponding to the graphs of FIGS. 12A–12C, with the wind conditions shown in FIG. 13A is the same as for that in FIG. 12A. In these figures, the sensor detects or measures the presence of detected DO in the water column, according to embodiments of the present invention. FIG. 13B illustrates the gradient measured at the north shore of Kennel Beach and FIG. 13C illustrates measurements taken at the south shore at Carolina Pines. In each case, the DO distribution in the water column indicates that there is an upwelling of low DO water.

Figure 14A:
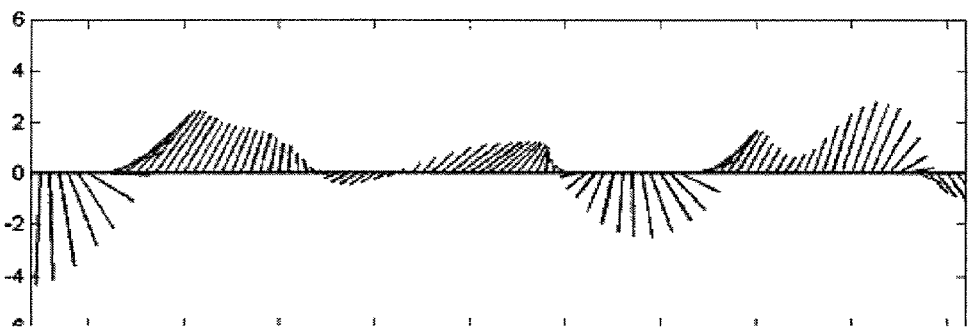
FIGS. 14A–14C are graphs similar to those of FIGS. 12A–12C but for a different time period during which there was a northerly wind or southerly wind (depending on the location of the automated system).
Figure 14B:
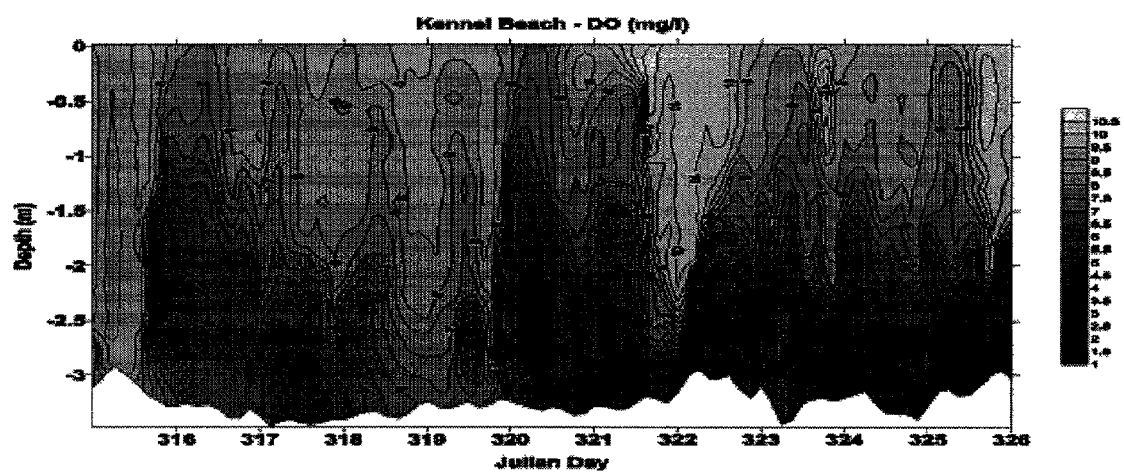
Figure 14C:
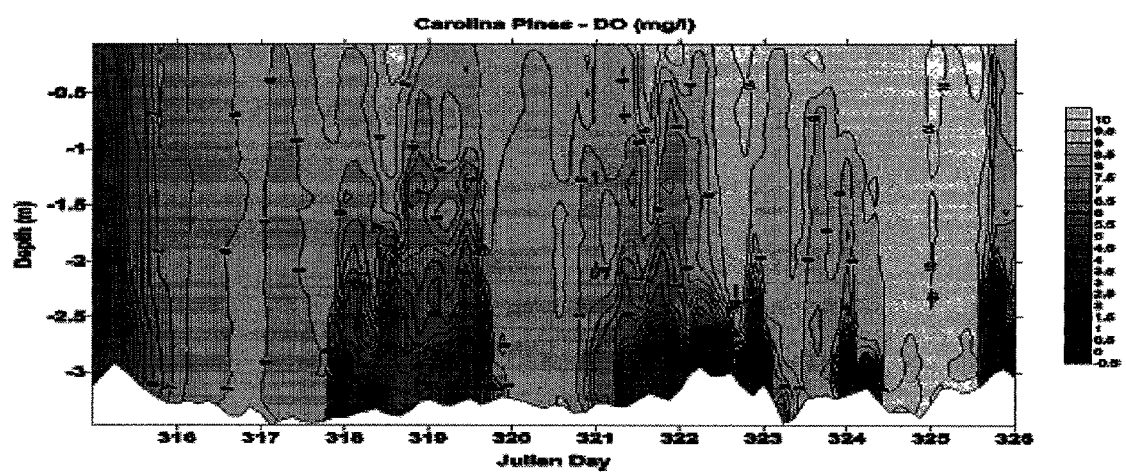

FIGS. 14A–14C are graphs similar to those of FIG. 12 but for a different time period where there is a northerly wind or southerly wind (depending on the location of the automated system). FIGS. 14B and 14C are graphs of salinity measured in the water column at the north shore of Kennel Beach and the south shore of Carolina Pines, respectively. FIG. 14B illustrates an upwelling of high salinity water with northerly winds while FIG. 14C illustrates an upwelling of high salinity water with southerly winds.

Figure 15A:
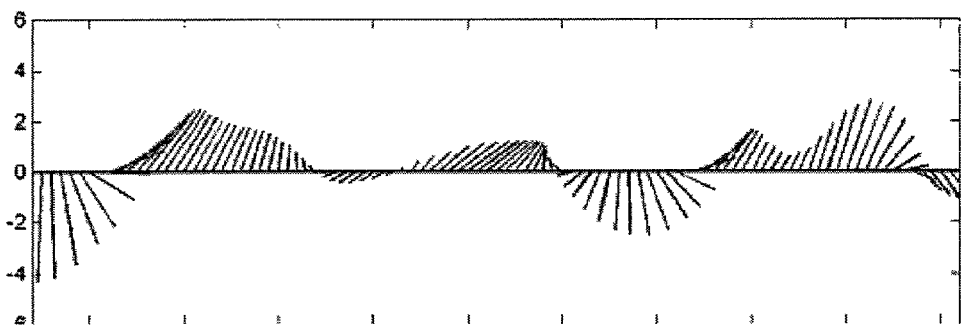
FIGS. 15A–15C correspond to FIGS. 14A–14C but illustrate the detected DO level in the water column. The wind conditions shown in FIG. 15A are the same as those shown in FIG. 14A.
Figure 15B:
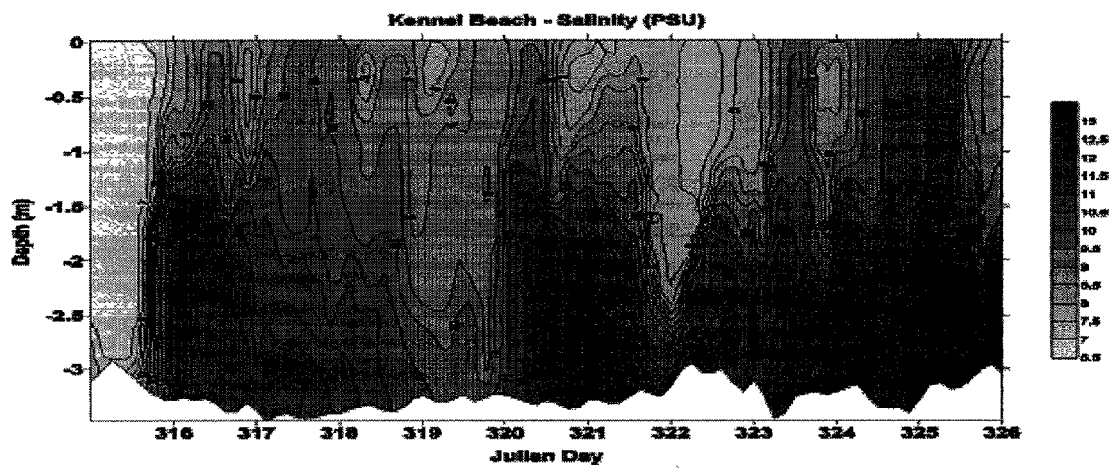
Figure 15C:
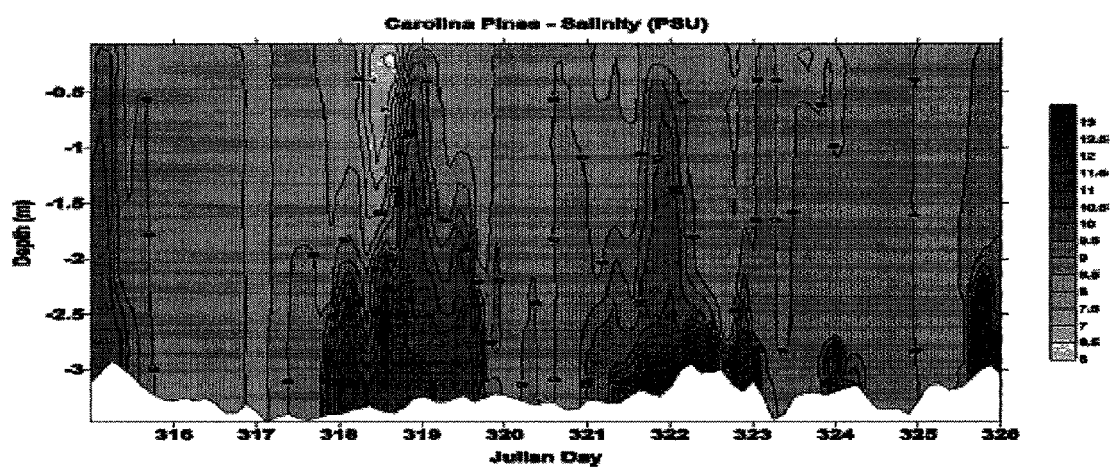

FIGS. 15A–15C correspond to FIGS. 14A–14C but illustrate the detected DO level in the water column. The wind conditions shown in FIG. 15A are the same as those shown in FIG. 14A. FIG. 15B illustrates the measurement results taken at the north shore of Kennel Beach and FIG. 15C illustrates the measurement results taken at the south shore of Carolina Pines. In each case there is an upwelling of low DO water resulting from a northerly wind (FIG. 15B) or a southerly wind (FIG. 15C).

Figure 16:
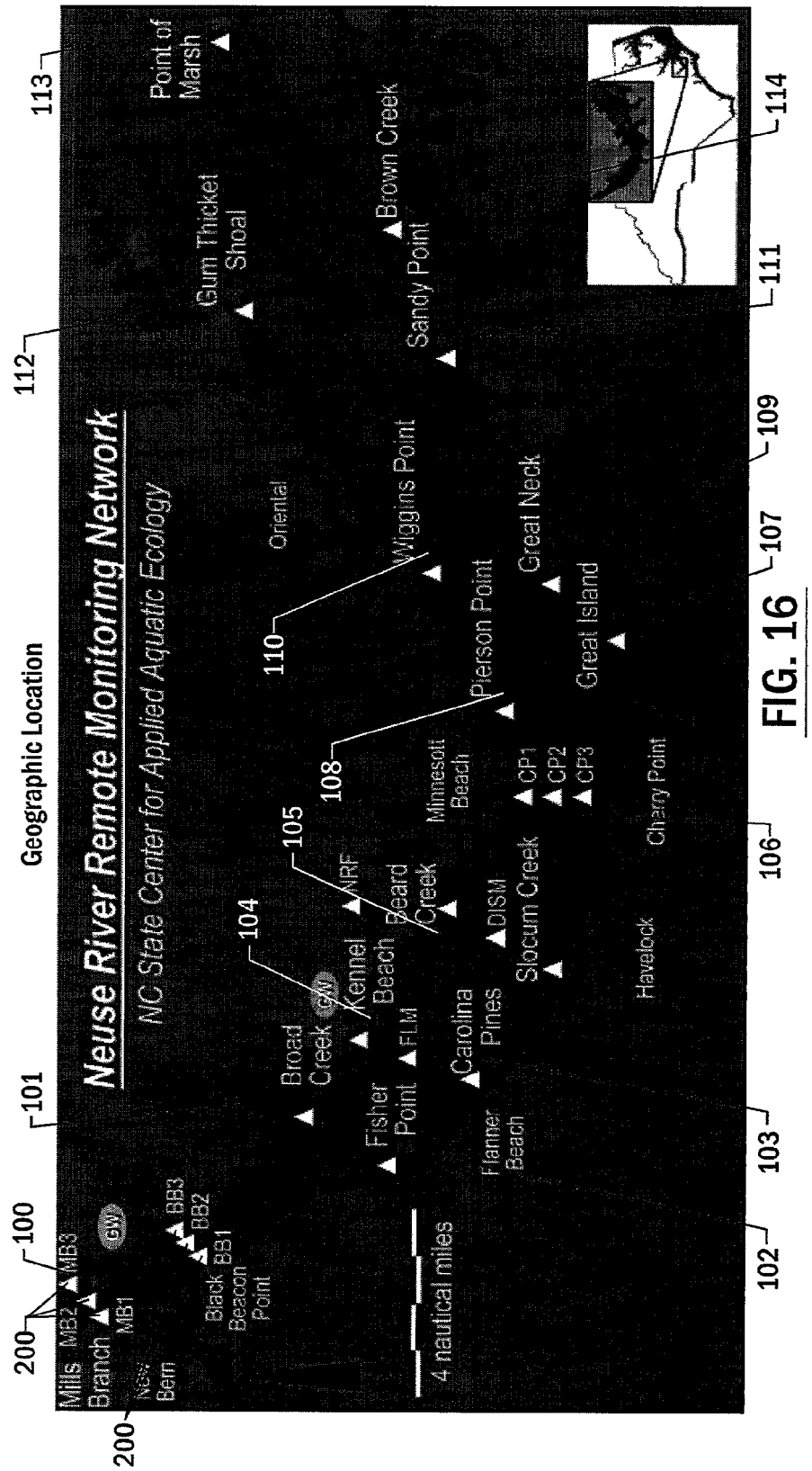
FIG. 16 is a map of locations for a multi-site automated water profiler system according to embodiments of the present invention.

FIG. 16 is a map of locations proposed for use in a multi-site automated water profiler system. An automated water profiling system 10 can be positioned in a plurality of different sampling sites in a related body of water. The data from each of the sites can be analyzed for correlations and/or the spatial distribution of the water conditions at the sites based on the dynamic water profiles obtained. The sites can be spaced apart (some may be located adjacent opposing banks) in a flowing (navigable) body of water to monitor regional correlations in water conditions such as in a waterway proximate an ocean inlet.

The number of dedicated monitored sites can be unlimited, but may include 3–10, or more. As shown, the sites 100–114 extend from upstream to downstream locations in a flowable body of water (the Neuse River is shown herein). Hydrological monitored sites (in FIG. 16) are represented by circles. Selected sites, such as, but not limited to, locations 100, 104, can include both metrological and hydrological measurement sensors while the other sites can be modified to with a less number of sensors to automatically detect and generate the hydrological without metrological data. The system may also include a number of nutrient monitoring sites 200 that are configured to monitor for additional parameters in the water over standard hydrological monitoring sites, these sites are illustrated by triangles in FIG. 16. For example, in the monitoring network shown in FIG. 16, at Mills Branch, with a hydrological monitoring station 100, there are three nutrient monitoring stations 200 positioned to substantially span the width of the waterway at this region, MB1, MB2, MB3. Black Beacon Point has three nutrient monitoring stations 200, BB1, BB2, BB3, and no hydrological station.

Each of the sites can be assigned an electronic identifier or identified by a GPS system that allows a central monitoring station to monitor, transmit and receive data from each of the sites. Also shown in FIG. 16 are sites 103

(Carolina Pines) and 104 (Kennel Beach) from which the data of FIGS. 12–14 were gathered.

Advantageously, the cost-effective water profiler systems allowed by the present system can allow increased locations to be numbered (5–10, or even 20 times as many) for a price relatively equal to that of one of the conventional automated systems. By monitoring at increased numbers of locations, additional potentially valuable scientific information can be obtained about the dynamic conditions along a body of water and the influence of environment and other factors on the water condition as the water moves from one location to another.

Figure 17:
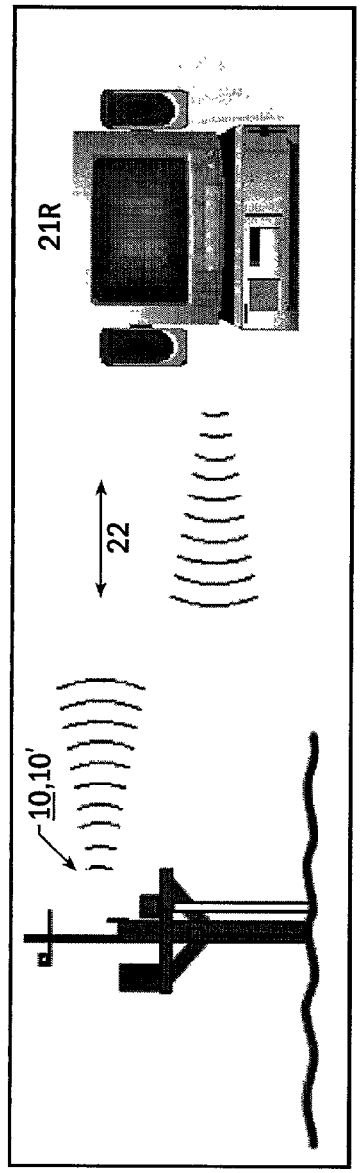
FIG. 17 is a schematic illustration of the operation of a dynamic monitoring system that can be visually dynamically presented on a computer network according to embodiments of the present invention.
Figure 17:
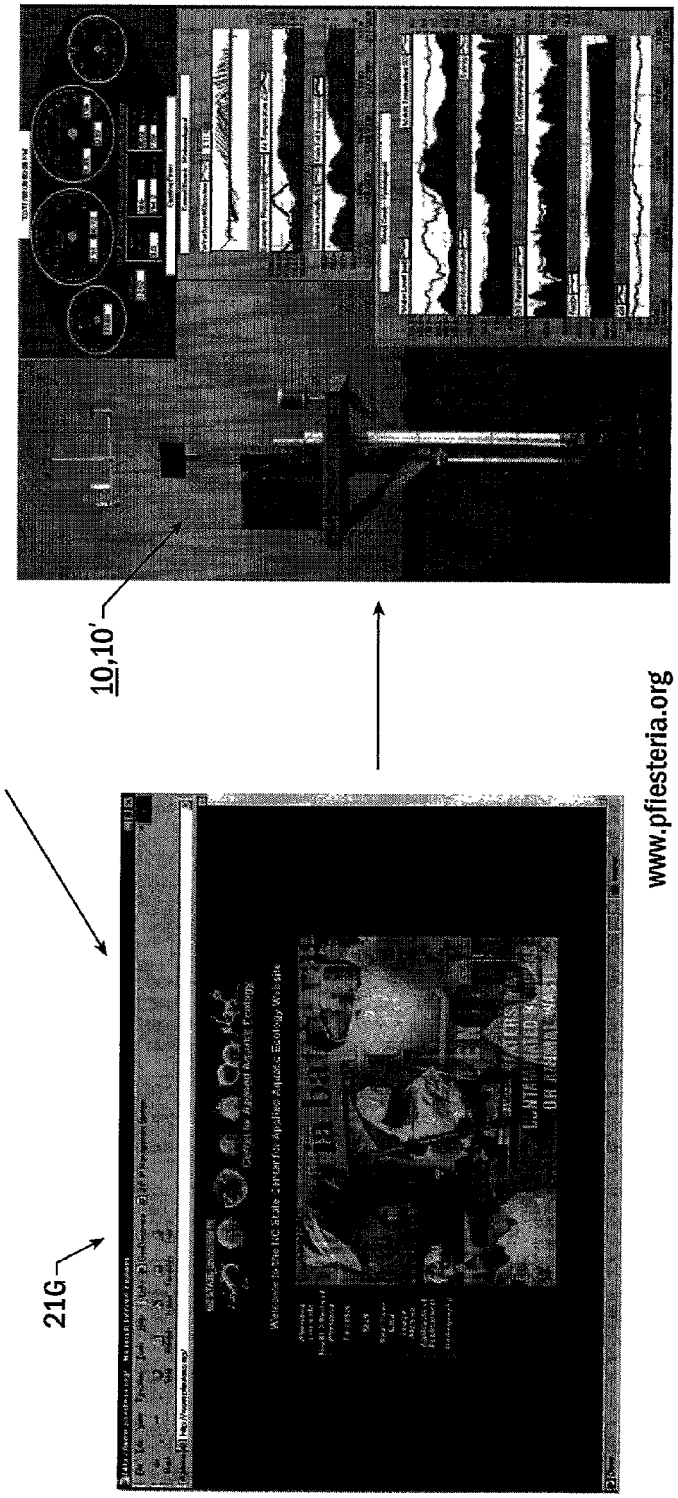

FIG. 17 is a schematic illustration of the operation of the transmission of data for a water profiler monitoring system that can track, over time, which can be transmitted to a remote computer station 21R and then uploaded and visually presented on a computer network 21G according to embodiments of the present invention. For this example, and the other embodiments discussed herein, the computer network can be a regional network, a defined computer network, or a global computer network such as the world wide web. The upload can update at desired intervals the measurement data in a visually easy to read format. The update can be performed such that the update is relayed to the desired computer network, such as the global computer network in substantially real time (or hourly, daily, or other desired interval).

Figure 18A:
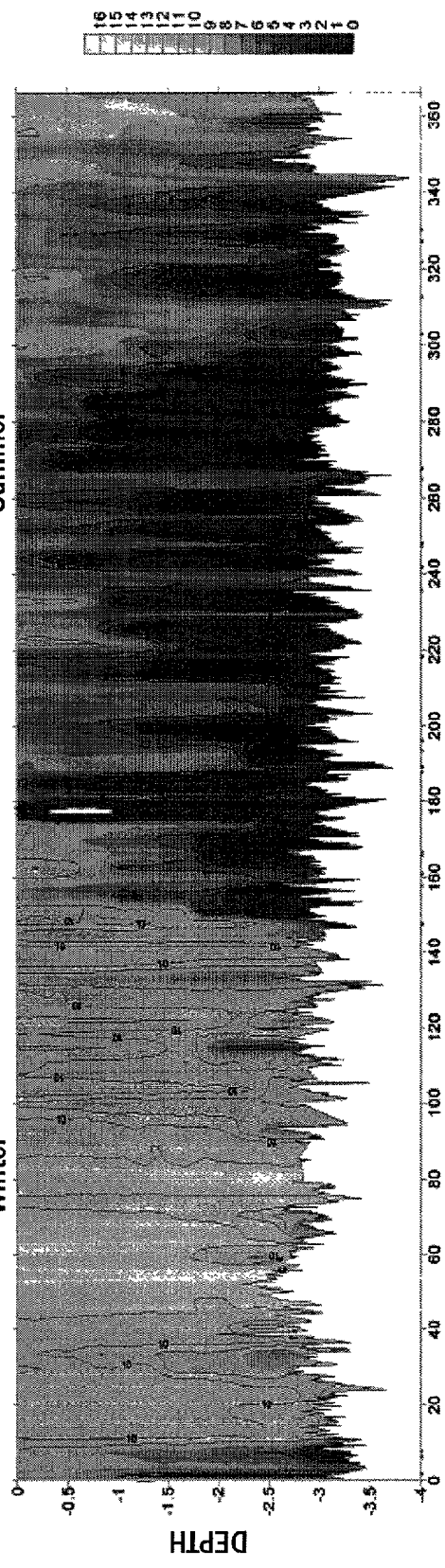
FIGS. 18A and 18B are a screen printouts of two sets of data showing a year trend analysis of depth of DO (FIG. 18A) and Salinity (FIG. 18B). Although shown in gray scale, color gradient graphics may also be used.
Figure 18B:
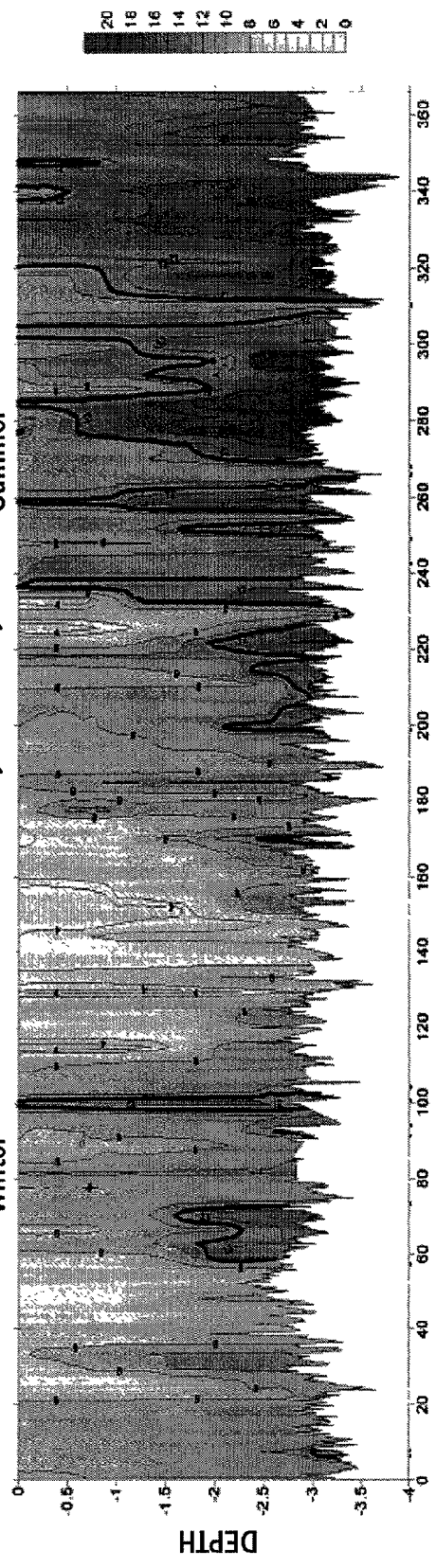
Figure 19:
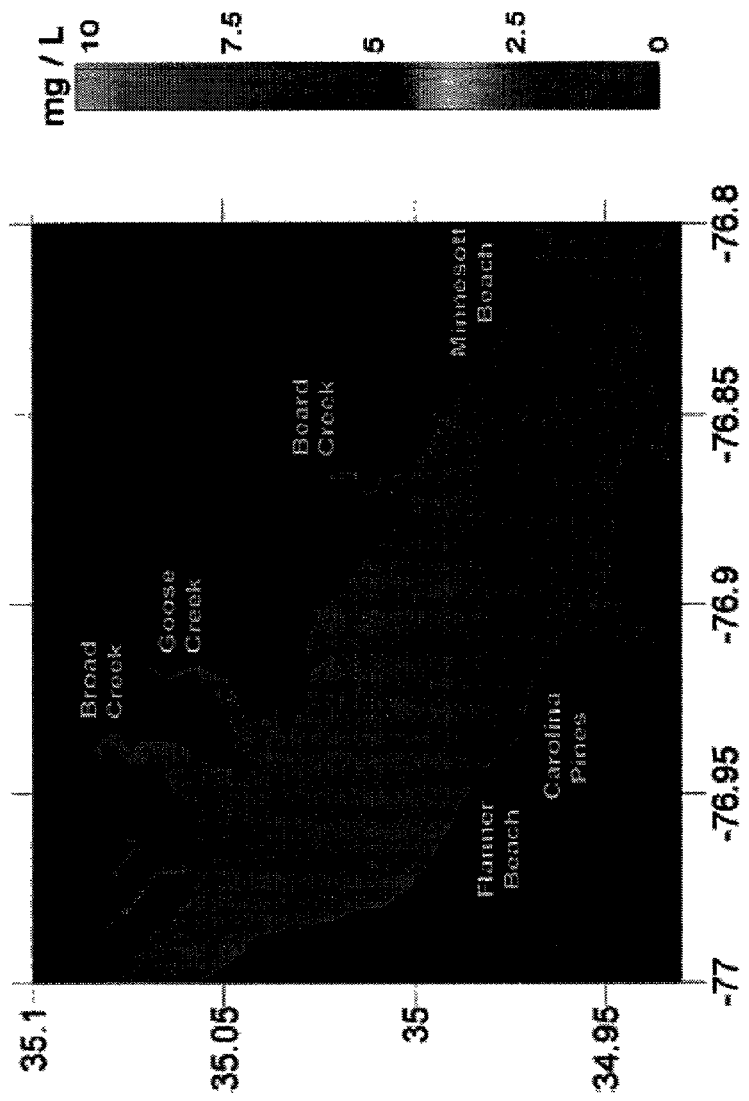
FIG. 19 is a spatial plot of DO that may be illustrated (if shown in color, red can be used to indicate regions having less than about 2.5 mg/L) that may be used as a predictor of fish kill in the monitored water system.

FIGS. 18A and 18B illustrate an annual trend analysis summary that can be generated according to certain embodiments of the present invention. FIG. 18A is a graph of depth versus DO values and day and FIG. 18B is a graph of salinity over the four seasons, with winter and summer shown (each can be shown in graduated color or gray scale, with the values corresponding to the legend on the right side of the figures). FIG. 19 is an example of a spatial plot of DO along a networked region of sites for Jun. 9, 2001, with areas less than 2.5 mg/L being associated with good predictors of a fish kill that occurred on Jun. 13, 2001.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A method for dynamically monitoring at least one parameter of interest in a liquid environment using a hydrological probe which is attached to a cable mounted on a spool of a winching system, comprising:
    controllably unwinding a quantity of cable to lower a hydrological probe into a liquid environment at a series of increasing incremental distances away from the surface of the liquid;
    obtaining first data measurements for at least one selected parameter of interest in the liquid environment at the selected distances;
    subsequently controllably unwinding a quantity of cable to lower a hydrological probe into the liquid environment at the series of increasing incremental distances away from the surface of the liquid;
    obtaining second data measurements forte at least one selected parameter of interest in the liquid environment at the selected distances after the first data measurements are obtained; and
    monitoring the liquid environment to generate a time-dependent liquid profile of the at least one parameter of interest based on the first and second data measurements,
    wherein said first and second obtaining steps include taking a reading at the surface of the liquid in variable height liquid environments.

2. A method according to claim 1, further comprising storing the hydrological probe in a submerged position.

3. A method for dynamically monitoring at least one parameter of interest in a liquid environment using a hydrological probe which is attached to a cable mounted on a spool of a winching system, comprising:
    controllably unwinding a quantity of cable to lower a hydrological probe into a liquid environment at a series of increasing incremental distances away from the surface of the liquid;
    obtaining first data measurements for at least one selected parameter of interest in the liquid environment at the selected distances;
    subsequently controllably unwinding a quantity of cable to lower a hydrological probe into the liquid environment at the series of increasing incremental distances away from the surface of the liquid;
    obtaining second data measurements for the at least one selected parameter of interest in the liquid environment at the selected distances after the first data measurements are obtained;
    monitoring the liquid environment to generate a time-dependent liquid profile of the at least one parameter of interest based on the first and second data measurements; and
    storing the hydroglogical probe such that the probe is held immersed in the liquid environment at a level sufficient to inhibit marine fouling after each of the first and second obtaining steps.

4. A method for dynamically monitoring at least one parameter of interest in a liquid environment using a hydrological probe which is attached to a cable mounted on a spool of a winching system, comprising:
    controllably unwinding a quantity of cable to lower a hydrological probe into a liquid environment at a series of increasing incremental distances away from the surface of the liquid;
    obtaining lint data measurements for at least one selected parameter of interest in the liquid environment at the selected distances;
    subsequently controllably unwinding a quantity of cable to lower a hydrological probe into the liquid environment at the series of increasing incremental distances away from the surface of the liquid;
    obtaining second data measurements for the at least one selected parameter of interest in the liquid environment at the selected distances after the first data measurements are obtained;
    monitoring the liquid environment to generate a time-dependent liquid profile of the at least one parameter of interest based on the first and second data measurements; and directing the hydrological probe into a guide tube disposed substantially vertically in the liquid environment at a series of increasing incremental distances away from the surface of the liquid so that the hydrological probe travels therein during the step of lowering.

5. A method according to claim 4, wherein the liquid environment is water and wherein the guide tube includes a plurality of apertures arranged and configured to allow liquid to enter therein at each of the desired measurement depths so that water representative of the water at the incremental measurement depths can be analyzed.

6. A method according to claim 4, wherein said first and second obtaining steps are carried out substantially concurrently at at least three different sites in different regions of a related body of water by different hydrological probes, said method further comprising:
    assigning location identifiers to the first, second, and third hydrological probe sites;
    relaying information from the first second end third sites to a central site; and
    analyzing the spatial distribution of the water conditions at the first, second, and third sites based on the dynamic water profiles obtained at the flint, second, and third sites.

7. A method according to claim 6, wherein said first, second, and third sites are spaced apart in a flowing body of water to monitor regional correlations in water conditions at a waterway proximate an ocean inlet.

8. A method according to claim 6, further comprising monitoring meteorological conditions at at least one of the hydrological probe sites concurrently with said first and second obtaining steps.

9. A method for dynamically monitoring at least one parameter of interest in a liquid environment using a hydrological probe which is attached to a cable mounted on a spool of a winching system, comprising:
    controllably unwinding a quantity of cable to lower a hydrological probe into a liquid environment at a series of increasing incremental distances away from the surface of the liquid;
    obtaining first data measurements for at least one selected parameter of interest in the liquid environment at the selected distances;
    subsequently controllably unwinding a quantity of cable to lower a hydrological probe into the liquid environment at the series of increasing incremental distances away from the surface of the liquid;
    obtaining second data measurements for the at least one selected parameter of interest in the liquid environment at the selected distances after the first data measurements are obtained; and
    monitoring the liquid environment to generate a rime-dependent liquid profile of the at least one parameter of interest based on the first and second data measurements,
    wherein the liquid environment comprises water) and wherein the incremental distances are incremental depths in a water column, and wherein the hydrological probe is held inside a guide tube as it travels up and down the water column.

10. A method according to claim 9, wherein the guide tube is substantially cylindrical and includes a plurality of axially spaced apart, axially elongated slots disposed about the perimeter of the guide tube at a plurality of positions along the length of the guide tube, The slots being configured in size and arranged in location about the length of the guide tube to allow water representative of the water at the incremental measurement depths to enter therein.

11. A method according to claim 10, wherein said guide tube is coated with an anti-fouling marine coating.

12. A method for dynamically monitoring at least one parameter of interest in a liquid environment using a hydrological probe which is attached to a cable mounted on a spool of a winching system, comprising:
    controllably unwinding a quantity of cable to lower a hydrological probe into a liquid environment at a series of increasing incremental distances away from the surface of the liquid;
    obtaining first data measurements for at least one selected parameter of interest in the liquid environment at the selected distances;
    subsequently controllably unwinding a quantity of cable to lower a hydrological probe into the liquid environment at the series of increasing incremental distances away from the surface of the liquid;
    obtaining second data measurements for the at least one selected parameter of interest in the liquid environment at the selected distances after the first data measurements are obtained;
    monitoring the liquid environment to generate a time-dependent liquid profile of the at least one parameter of interest based on the first and second data measurements; and
    automatically measuring the water level of the surface of the water proximate in time to said first and second obtaining steps.

13. A method for dynamically monitoring at least one parameter of interest in a liquid environment using a hydrological probe which is attached to cable configured to be wrapped around a spool of a winching system comprising:
    controllably winding a quantity of cable from the winching system to raise a hydrological probe in a liquid environment at a series of increasing incremental distances above the bottom of the liquid;
    obtaining first data measurements for at least one selected parameter of interest in the liquid environment at the selected distances;
    repeating said winding step and then obtaining second data measurements for the at least one selected parameter of interest in the liquid environment at the selected distances after the first data measurements are obtained; and
    monitoring the liquid environment to define a time-dependent liquid profile of the at least one parameter of interest based on the first and second data measurements,
    wherein the winching system is powered by a battery which has a useful service life of at least 30 days when said first and second obtaining steps are performed so as to obtain at least about 4 measurements of the water column during a 24 hour period,
    wherein said liquid environment is a body of water, and wherein said first and second obtaining steps are automatically carried out so as to generate data measurements at about 3 hour intervals,
    wherein the intervals at which the data measurements are obtained are decreased or increased based on an in situ measurement of local conditions.

14. A method according to claim 13, wherein said first and second obtaining steps are automatically repeated so as to generate updated dynamic water profiles about every three hours for at least 1 week to 1 month.

15. A method according to claim 13, wherein the liquid environment is a water environment, and wherein said first and second obtaining steps are performed so that the measurements arc taken at depths spaced at no greater than about every 1.0 m from the bottom of the water column to the surface of the water column.

16. A method according to claim 13, wherein said raising step is automatically carried out such that the hydrological probe takes a first measurement and then is raised for a user defined interval of at least about 30 seconds to a second depth, pauses to take a measurement at a second depth, continues up for about another user defined interval of at least about 30 seconds to a third depth, pauses to take a measurement at the third depth, continues up for about another user defined interval of at least about 30 seconds to a fourth depth, and pauses to take a measurement at the fourth depth.

17. A method according to claim 13, wherein the meted is carried out at a plurality of different sites, each having a geographic identifier associated therewith, said method further transmitting the data associated with the liquid profiles from the different sites to a central remote collection site.

18. A method according to claim 13, further comprising the step of relaying the data to a remote site for monitoring.

19. A method according to claim 18, further comprising the step of posting the data as a gradient graph display of measured parameters over a suitable time period to a global computer network site proximate in time to the data acquisition.

20. A method according to claim 13, wherein the liquid environment is a flowing body of water, and wherein said first and second obtaining steps are carried out substantially concurrently at at least three different sites in different regions of a related body of water by different hydrological probes, said method further comprising:
  assigning location identifiers to the first, second, and third hydrological probe sites;
  relaying information from the first second and third sites to a central site; and
  analyzing the spatial distribution of the water conditions at the first, second, and third sites based on the dynamic water profiles obtained at the first, second, and third sites.

21. A method according to claim 20, wherein said first, second, and third sites are spaced apart in a flowing body of water to monitor regional correlations in water conditions at a waterway proximate an ocean inlet.

22. A method according to claim 20, further comprising monitoring meteorological conditions at at least one of the hydrological probe sites concurrently with said first and second obtaining steps.

23. A method for dynamically monitoring at least one parameter of interest in a liquid environment using a hydrological probe which is attached to cable configured to be wrapped around a spool of a winching system comprising:
  controllably winding a quantity of cable from the winching system to raise a hydrological probe in a liquid environment at a series of increasing incremental distances above the bottom of the liquid;
  obtaining first data measurements for at least one selected parameter of interest in the liquid environment at the selected distances;
  repeating said winding step and then obtaining second data measurements for the at least one selected parameter of interest in the liquid environment at the selected distances after the first data measurements are obtained;
  monitoring the liquid environment to define a time-dependent liquid profile of the at least one parameter of interest based on the first and second data measurements,
  wherein the winching system is powered by a battery which has a useful service life of at least 30 days when said first and second obtaining steps are performed so as to obtain at least about 4 measurements of the water column during a 24 hour period, and
  directing the hydrological probe to travel up and down the water column inside a guide tube,
  wherein the liquid environment comprises a water column, and wherein the incremental distances are incremental depths in a water column, and wherein the data measurements of said first andsecond obtaining steps comprise dwelling at a measurement depth at about every 0.5 m from the bottom of the water column to the water level surface.

24. A method according to claim 23, wherein said guide tube is substantially cylindrical and includes a plurality of axially spaced apart, axially elongated slots disposed about the perimeter of the guide tube at a plurality of positions along the length of the guide tube, the slots being configured in size and arranged in location about the length of the guide tube to allow water representative of die water at the incremental measurement depths to enter therein.

25. A method according to claim 24, wherein said guide tube is coated with an anti-fouling marine coating.

26. A method for dynamically monitoring at least one parameter of interest in a liquid environment using a hydrological probe which is attached to cable configured to be wrapped around a spool of a winching system comprising:
  controllably winding a quantity of cable from the winching system to raise a hydrological probe in a liquid environment at a series of increasing incremental distances above the bottom of the liquid;
  obtaining first data measurements for at least one selected parameter of interest in the liquid environment at the selected distances;
  repeating said winding step and then obtaining second data measurements for the at least one selected parameter of interest in the liquid environment at the selected distances after the first data measurements are obtained;
  monitoring the liquid environment to define a time-dependent liquid profile of the at least one parameter of interest based on the first and second data measurements; and
  automatically measuring the water level of the surface of the water column proximate in time to said first and second obtaining steps.

27. A method for dynamically monitoring at least one parameter of interest in a liquid environment using a hydrological probe which is attached to a cable mounted on a spool of a winching system, comprising:
  controllably unwinding a quantity of cable to lower a hydrological probe into a liquid environment at a series of increasing incremental distances away from the surface of the liquid using a motor with a torque of about 50 lb-in or less;
  obtaining first data measurements for at least one selected parameter of interest in the liquid environment at the selected distances;
  subsequently controllably unwinding a quantity of cable to lower a hydrological probe into the liquid environment at the series of increasing incremental distances away from the surface of the liquid, using the motor with about 50 lb-in of torque or less;

obtaining second data measurements for the at least one selected parameter of interest in the liquid environment at the selected distances after the first data measurements are obtained; and monitoring the liquid environment to generate a time-dependent liquid profile of the at least one parameter of interest based on the first and second data measurements, wherein the winching system is configured as a compact non-floating assembly that is mountable to a fixed structure located in a body of liquid, and wherein, in use, the battery is externally accessible, and wherein said first and second obtaining steps include taking a reading at the surface of the liquid in variable height liquid environments.

28. A method according to claim 27, wherein the motor is geared, and wherein the unwinding steps are carried out using the geared motor to deploy the cable during the entire unwinding and winding operations.

29. A method according to claim 27, wherein the compact assembly includes a generally rectangular housing that encases the motor and battery, the housing having a length of about 12 inches or less, and wherein the spool is held generally vertically and has a length of about 12 inches or less and resides under the housing in communication with the motor, and wherein the compact assembly has a weight that is about 25 pounds or less.

30. A method according to claim 29, wherein the motor has an rpm rating of less than about 15 rpm, the method further comprising employing a torque limiter in communication with the motor and spool to inhibit over-torque operation.

31. A method for dynamically monitoring at least one parameter of interest in a liquid environment using a hydrological probe which is attached to cable configured to be wrapped around a spool of a winching system comprising;
controllably winding a quantity of cable from the winching system to raise a hydrological probe in a liquid environment at a series of increasing incremental distances above the bottom of the liquid using a motor having about a 1/60 or lower horsepower rating;
obtaining first data measurements for at least one selected parameter of interest in the liquid environment at the selected distances;
repeating said winding step and then obtaining second data measurements for the at least one selected parameter of interest in the liquid environment at the selected distances after the first data measurements are obtained; and
monitoring the liquid environment to define a time-dependent liquid profile of the at least one parameter of interest based on the first and second data measurements,
wherein the motor is powered by a 12V battery, and wherein the motor is about a 1/1200 HP, 50 lb-in, 0.45 rpm rated motor,
wherein the winching system is configured as a compact non-floating assembly that is mountable to a fixed structure located in a body of liquid, and wherein, in use, the battery is externally accessible, and wherein said first and second obtaining steps include taking a reading at the surface of the liquid in variable height liquid environments.

32. A method according to claim 31, wherein the motor is powered by a 12V battery, and wherein the motor is about a 1/60 HP, 40 lb-in, 12 rpm rated motor.

33. A method according to claim 31, wherein the motor is powered by a 12V battery, and wherein the motor is about a 1/1200 HP, 50 lb-in, 0,45 rpm rated motor.

34. A method according to claim 31, wherein the compact assembly includes a generally rectangular housing that encases the motor and battery, the housing having a length of about 12 inches or less, and wherein the spool is held generally vertically and has a length of about 12 inches or less and resides under the housing in communication with the motor, and wherein the compact assembly has a weight that is about 25 pounds or less.

35. A method according to claim 31, wherein the motor has an rpm rating of less than about 15 rpm, the method further comprising employing a torque limiter in communication with the motor and spool to inhibit over-torque operation.

36. A method according to claim 31, wherein the motor is geared, and wherein the unwinding steps are carried out using the geared motor to deploy the cable during the entire unwinding and winding operations.

37. A method for dynamically monitoring at least one parameter of interest in a liquid environment using a hydrological probe which is attached to cable configured to be wrapped around a spool of a winching system comprising:
controllably winding a quantity of cable from the winching system to raise a hydrological probe in a liquid environment at a series of increasing incremental distances above the bottom of the liquid;
obtaining first data measurements for at least one selected parameter of interest in the liquid environment at the selected distances;
repeating said winding step and then obtaining second data measurements for the at least one selected parameter of interest in the liquid environment at the selected distances after the first data measurements are obtained; and
monitoring the liquid environment to define a time-dependent liquid profile of the at least one parameter of interest based on the first and second data measurements,
wherein the winching system is powered by a battery which has a useful service life of at least 30 days when said first and second obtaining steps are performed so as to obtain at least about 4 measurements of the water column during a 24 hour period,
wherein said obtaining steps include taking a reading at the surface of the liquid in variable height liquid environments.

38. A method for dynamically monitoring at least one parameter of interest in a liquid environment using a hydrological probe which is attached to cable configured to be wrapped around a spool of a winching system comprising:
controllably winding a quantity of cable from the winching system to raise a hydrological probe in a liquid environment at a series of increasing incremental distances above the bottom of the liquid;
obtaining first data measurements for at least one selected parameter of interest in the liquid environment at the selected distances;
repeating said winding step and then obtaining second data measurements for the at least one selected parameter of interest in the liquid environment at the selected distances after the first data measurements are obtained; and monitoring the liquid environment to define a time-dependent liquid profile of the at least one parameter of interest based on the first and second data measurements, lowering the probe to a subsurface storage position adjacent the bottom of the liquid environment being analyzed during periods of inactivity, and wherein the steps of raising and lowering are carried out to wind and unwind about 30–80 feet of cable, wherein the winching system is powered by a battery which has a useful service life of at least 30 days when said first and second obtaining steps are performed so as to obtain at least about 4 measurements of the water column during a 24 hour period.

39. A method according to claim 38, wherein said first obtaining step has a cycle time of less than about 40–90 minutes from initiation of the first measurement at the first depth to the last measurement at the last measurement depth.

40. A method according to claim 38, wherein said liquid environment is a water environment, and wherein said first obtaining step is carried out such that a plurality of measurements are taken at a plurality of depths in a water column of less than about 25 m during an elapsed time of about 20–40 minutes or less.

41. A method for dynamically monitoring at least one parameter of interest in a liquid environment using a hydrological probe which is attached to cable configured to be wrapped around a spool of a winching system comprising:

controllably winding a quantity of cable from the winching system to raise a hydrological probe in a liquid environment at a series of increasing incremental distances above the bottom of the liquid;

obtaining first data measurements for at least one selected parameter of interest in the liquid environment at the selected distances;

repeating said winding step and then obtaining second data measurements for the at least one selected parameter of interest in the liquid environment at the selected distances after the first data measurements are obtained; and monitoring the liquid environment to define a time-dependent liquid profile of the at least one parameter of interest based on the first and second data measurements, wherein the winching system is powered by a battery which has a useful service life of at least 30 days when said first and second obtaining steps are performed so as to obtain at least about 4 measurements of the water column during a 24 hour period, wherein the liquid environment is a water environment, and wherein the method further comprises storing the hydrological probe after said first and second obtaining steps when not in use such that it is held immersed in the liquid environment at a level sufficient to inhibit marine fouling.

42. A method for dynamically monitoring at least one parameter of interest in a liquid environment using a hydrological probe which is attached to cable configured to be wrapped around a spool of a winching system comprising:

controllably winding a quantity of cable from the winching system to raise a hydrological probe in a liquid environment at a series of increasing incremental distances above the bottom of the liquid;

obtaining first data measurements for at least one selected parameter of interest in the liquid environment at the selected distances;

repeating said winding step and then obtaining second data measurements for the at least one selected parameter of interest in the liquid environment at the selected distances after the first data measurements are obtained;

monitoring the liquid environment to define a time-dependent liquid profile of the at least one parameter of interest based on the first and second data measurements, wherein the winching system is powered by a battery which has a useful service life of at least 30 days when said first and second obtaining steps are performed so as to obtain at least about 4 measurements of the water column during a 24 hour period; and directing the hydrological probe into a guide tube disposed substantially vertically in the liquid environment at a series of increasing incremental distances away from the surface of the liquid so that the hydrological probe travels therein during the step of lowering.

43. A method according to claim 42, wherein the liquid environment is water and wherein the guide tube includes a plurality of apertures arranged and configured to allow liquid to enter therein at each of the desired measurement depths so that water representative of the water at the incremental measurement depths can be analyzed.

* * * * *

UNITED STATES PATENT AND TRADEMARK OFFICE
CERTIFICATE OF CORRECTION

PATENT NO. : 7,040,157 B2
APPLICATION NO. : 10/208504
DATED : May 9, 2006
INVENTOR(S) : Glasgow, Jr. et al.

It is certified that error appears in the above-identified patent and that said Letters Patent is hereby corrected as shown below:

On the Title Page:
Section 12 should read -- Reed et al. --

Section 75 should read -- Robert E. Reed, Raleigh, NC (US); JoAnn Burkholder, Raleigh, NC (US); David C. Toms, Raleigh, NC (US); Howard Glasgow, Jr., Bahama, NC (US) --

Column 20,
Line 5 should read -- obtaining second data measurements for the at least one --

Line 53 should read --obtaining first data measurements for at least one selected --

Column 21,
Line 19 should read -- relaying information from the first second and third sites --

Line 23 should read -- water profiles obtained at the first, second, and third --

Line 57 should read -- wherein the liquid environment comprises water, and --

Column 23.
Line 4 should read -- surements are taken at depths spaced at no greater than about --.

Line 18 should read -- 17. A method according to claim 13, wherein the method is --

UNITED STATES PATENT AND TRADEMARK OFFICE
CERTIFICATE OF CORRECTION

PATENT NO. : 7,040,157 B2
APPLICATION NO. : 10/208504
DATED : May 9, 2006
INVENTOR(S) : Glasgow, Jr. et al.

It is certified that error appears in the above-identified patent and that said Letters Patent is hereby corrected as shown below:

Column 24,
Line 15 should read -- measurements of said first and second obtaining steps --

Line 25 should read -- tube to allow water representative of the water at the --

Signed and Sealed this

Fifth Day of December, 2006

JON W. DUDAS
*Director of the United States Patent and Trademark Office*